United States Patent
Fukuoka et al.

(10) Patent No.: US 10,658,707 B2
(45) Date of Patent: May 19, 2020

(54) DETECTION SYSTEM

(71) Applicant: Panasonic Intellectual Property Management Co., Ltd., Osaka (JP)

(72) Inventors: Ayumu Fukuoka, Osaka (JP); Kazuyoshi Honda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 329 days.

(21) Appl. No.: 15/646,681

(22) Filed: Jul. 11, 2017

(65) Prior Publication Data

US 2018/0026313 A1    Jan. 25, 2018

(30) Foreign Application Priority Data

Jul. 19, 2016   (JP) .................. 2016-141438

(51) Int. Cl.
| | | |
|---|---|---|
| *H01M 10/42* | (2006.01) | |
| *G01N 27/12* | (2006.01) | |
| *G01N 33/00* | (2006.01) | |
| *H01M 10/48* | (2006.01) | |
| *H01M 2/10* | (2006.01) | |
| *H01M 10/0525* | (2010.01) | |
| *H01M 10/0562* | (2010.01) | |

(52) U.S. Cl.
CPC ...... *H01M 10/4228* (2013.01); *G01N 27/125* (2013.01); *G01N 33/0044* (2013.01); *H01M 2/1022* (2013.01); *H01M 2/1072* (2013.01); *H01M 10/0525* (2013.01); *H01M 10/0562* (2013.01); *H01M 10/48* (2013.01); *G01N 27/12* (2013.01); *H01M 2300/0068* (2013.01)

(58) Field of Classification Search
None
See application file for complete search history.

(56) References Cited

U.S. PATENT DOCUMENTS

| | | | |
|---|---|---|---|
| 10,365,257 B2 * | 7/2019 | Fukuoka | G01N 31/224 |
| 2003/0072998 A1 * | 4/2003 | Fredriksson | H01M 2/0207 |
| | | | 429/210 |
| 2005/0260493 A1 * | 11/2005 | Frederiksson | H01M 10/282 |
| | | | 429/210 |
| 2010/0297479 A1 | 11/2010 | Tsuchida et al. | |
| 2012/0015220 A1 * | 1/2012 | Kawaoka | H01M 10/052 |
| | | | 429/90 |
| 2014/0370338 A1 * | 12/2014 | Lim | H01M 2/348 |
| | | | 429/62 |
| 2017/0309968 A1 * | 10/2017 | Komori | H01M 10/4285 |
| 2017/0309975 A1 * | 10/2017 | Iwamoto | H01M 10/52 |

FOREIGN PATENT DOCUMENTS

JP    2009-193727    8/2009

* cited by examiner

*Primary Examiner* — Rena Dye Cronin
(74) *Attorney, Agent, or Firm* — Greenblum & Bernstein, P.L.C.

(57) ABSTRACT

A detection system includes a power generation element; a first outer cover body enveloping the power generation element; a second outer cover body located between the power generation element and the first outer cover body, and enveloping the power generation element; a first space section enclosed by the first outer cover body and the second outer cover body; a second space section enclosed by the second outer cover body; and a detection unit that detects "a gas in the first space section" and "a gas in the second space section."

15 Claims, 27 Drawing Sheets

FIG. 10

| | DETECTION RESULT IN FIRST SPACE SECTION | DETECTION RESULT IN SECOND SPACE SECTION | DETERMINATION RESULT | |
|---|---|---|---|---|
| | DETECTION OF OUTSIDE ATMOSPHERE | DETECTION OF FIRST GAS | BREAKAGE STATE OF FIRST OUTER COVER BODY | BREAKAGE STATE OF SECOND OUTER COVER BODY |
| CASE A-10 | NOT DETECTED | NOT DETECTED | NOT BROKEN | NOT BROKEN |
| CASE B-10 | DETECTED | NOT DETECTED | BROKEN | NOT BROKEN |
| CASE C-10 | NOT DETECTED | DETECTED | NOT BROKEN | BROKEN |
| CASE D-10 | DETECTED | DETECTED | BROKEN | BROKEN |

FIG. 11

| | DETECTION RESULT IN FIRST SPACE SECTION | | DETECTION RESULT IN SECOND SPACE SECTION | DETERMINATION RESULT | |
|---|---|---|---|---|---|
| | DETECTION OF OUTSIDE ATMOSPHERE | DETECTION OF SECOND GAS | DETECTION OF FIRST GAS | BREAKAGE STATE OF FIRST OUTER COVER BODY | BREAKAGE STATE OF SECOND OUTER COVER BODY |
| CASE A-20 | NOT DETECTED | NOT DETECTED | NOT DETECTED | NOT BROKEN | NOT BROKEN |
| CASE B-20 | DETECTED | NOT DETECTED | NOT DETECTED | BROKEN | NOT BROKEN |
| CASE C-20 | NOT DETECTED | DETECTED | DETECTED | NOT BROKEN | BROKEN |
| CASE C-21 | NOT DETECTED | DETECTED | NOT DETECTED | NOT BROKEN | BROKEN |
| CASE C-22 | NOT DETECTED | NOT DETECTED | DETECTED | NOT BROKEN | BROKEN |
| CASE D-20 | DETECTED | DETECTED | DETECTED | BROKEN | BROKEN |
| CASE D-21 | DETECTED | DETECTED | NOT DETECTED | BROKEN | BROKEN |
| CASE D-22 | DETECTED | NOT DETECTED | DETECTED | BROKEN | BROKEN |

FIG. 12

| | DETECTION RESULT IN FIRST SPACE SECTION | | DETECTION RESULT IN SECOND SPACE SECTION | | DETERMINATION RESULT | |
|---|---|---|---|---|---|---|
| | DETECTION OF OUTSIDE ATMOSPHERE | DETECTION OF SECOND GAS | DETECTION OF FIRST GAS | DETECTION OF OUTSIDE ATMOSPHERE | BREAKAGE STATE OF FIRST OUTER COVER BODY | BREAKAGE STATE OF SECOND OUTER COVER BODY |
| CASE A-30 | NOT DETECTED | NOT DETECTED | NOT DETECTED | NOT DETECTED | NOT BROKEN | NOT BROKEN |
| CASE B-30 | DETECTED | NOT DETECTED | NOT DETECTED | NOT DETECTED | BROKEN | NOT BROKEN |
| CASE C-30 | NOT DETECTED | DETECTED | DETECTED | NOT DETECTED | NOT BROKEN | BROKEN |
| CASE D-30 | DETECTED | DETECTED | DETECTED | DETECTED | BROKEN | BROKEN |
| CASE D-31 | DETECTED | DETECTED | NOT DETECTED | DETECTED | BROKEN | BROKEN |
| CASE D-32 | DETECTED | NOT DETECTED | DETECTED | DETECTED | BROKEN | BROKEN |
| CASE D-33 | DETECTED | NOT DETECTED | NOT DETECTED | DETECTED | BROKEN | BROKEN |

FIG. 19

| | DETECTION RESULT IN FIRST SPACE SECTION | | DETERMINATION RESULT | |
|---|---|---|---|---|
| | DETECTION OF OUTSIDE ATMOSPHERE | DETECTION OF SECOND GAS | BREAKAGE STATE OF FIRST OUTER COVER BODY | BREAKAGE STATE OF SECOND OUTER COVER BODY |
| CASE A-40 | NOT DETECTED | NOT DETECTED | NOT BROKEN | NOT BROKEN |
| CASE B-40 | DETECTED | NOT DETECTED | BROKEN | NOT BROKEN |
| CASE C-40 | NOT DETECTED | DETECTED | NOT BROKEN | BROKEN |
| CASE D-40 | DETECTED | DETECTED | BROKEN | BROKEN |

FIG. 27

| | DETECTION RESULT IN SECOND SPACE SECTION | | DETERMINATION RESULT | |
|---|---|---|---|---|
| | DETECTION OF OUTSIDE ATMOSPHERE | DETECTION OF FIRST GAS | BREAKAGE STATE OF FIRST OUTER COVER BODY | BREAKAGE STATE OF SECOND OUTER COVER BODY |
| CASE A-50 | NOT DETECTED | NOT DETECTED | NOT BROKEN | NOT BROKEN |
| CASE C-50 | NOT DETECTED | DETECTED | NOT BROKEN | BROKEN |
| CASE D-50 | DETECTED | DETECTED | BROKEN | BROKEN |
| CASE D-51 | DETECTED | NOT DETECTED | BROKEN | BROKEN |

DETECTION SYSTEM

BACKGROUND

1. Technical Field

The present disclosure relates to a detection system.

2. Description of the Related Art

Japanese Patent No. 5459319 discloses a cell containing a material which chemically reacts with hydrogen sulfide and the electrical resistance of which varies; and a hydrogen sulfide detection unit.

SUMMARY

In related art, it is desirable to increase detection accuracy of the breakage state of an outer cover member enveloping a power generation element.

In one general aspect, the techniques disclosed here feature a detection system including a power generation element; a first outer cover body enveloping the power generation element; a second outer cover body located between the power generation element and the first outer cover body, and enveloping the power generation element; a first space section enclosed by the first outer cover body and the second outer cover body; a second space section enclosed by the second outer cover body; and a detection unit that detects a gas in the first space section and a gas in the second space section.

With the present disclosure, the detection accuracy of the breakage state of the outer cover member enveloping the power generation element can be increased.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 10 illustrates a determination method of a determination unit according to the second embodiment;

FIG. 11 illustrates a determination method of the determination unit according to the second embodiment;

FIG. 12 illustrates a determination method of the determination unit according to the second embodiment;

FIG. 19 illustrates a determination method of a determination unit according to the fourth embodiment;

FIG. 27 illustrates a determination method of a determination unit according to the sixth embodiment.

DETAILED DESCRIPTION

Embodiments of the present disclosure are described below with reference to the drawings.

First Embodiment

Figure 1:
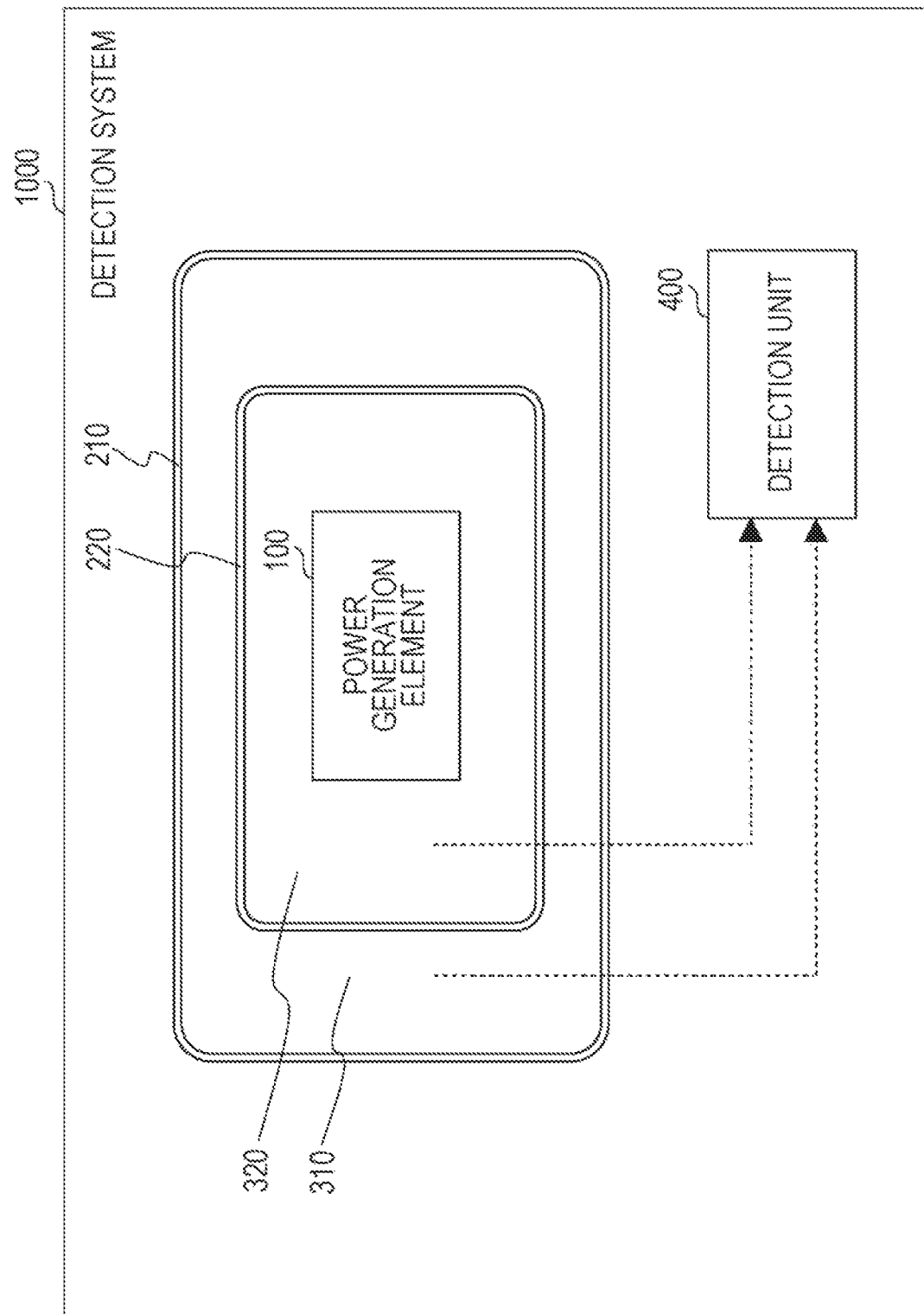
FIG. 1 illustrates a general configuration of a detection system according to a first embodiment.

FIG. 1 illustrates a general configuration of a detection system 1000 according to a first embodiment.

The detection system 1000 according to the first embodiment includes a power generation element 100, a first outer cover body 210, a second outer cover body 220, a first space section 310, a second space section 320, and a detection unit 400.

The first outer cover body 210 envelops the power generation element 100 and the second outer cover body 220.

The second outer cover body 220 is located between the power generation element 100 and the first outer cover body 210. The second outer cover body 220 envelops the power generation element 100.

The first space section 310 is a space enclosed (for example, hermetically sealed) by the first outer cover body 210 and the second outer cover body 220.

The second space section 320 is a space enclosed (for example, hermetically sealed) by the second outer cover body 220.

The detection unit 400 detects "a gas in the first space section 310" and "a gas in the second space section 320."

With the above-described configuration, the detection accuracy of the breakage state of the outer cover member enveloping the power generation element 100 can be increased. To be specific, the presence of breakage of the first outer cover body 210 and the second outer cover body 220 can be detected on the basis of the detection result of the gas in the first space section 310 and the detection result of the gas in the second space section 320. Accordingly, the generation of breakage of the first outer cover body 210 and the second outer cover body 220 can be detected with high accuracy at an early stage. Hence, for example, if at least one of the first outer cover body 210 and the second outer cover body 220 is broken, a measure of stopping use of the power generation element 100 or another measure can be executed at an early stage. Accordingly, the safety of the system using the power generation element 100 can be increased.

Also, with the above-described configuration, the first outer cover body 210 and the second outer cover body 220 can provide a double outer cover structure. Accordingly, resistance to an impact from the outside of the outer cover bodies, and impermeability to water can be increased. Further, a generated gas (for example, hydrogen sulfide gas) generated from the power generation element 100 over long-term use of the power generation element 100 can be prevented from leaking to the outside.

In the first embodiment, the power generation element 100 may be a single battery cell.

Alternatively, the power generation element 100 may be a multilayer battery in which a plurality of single battery cells are stacked.

Still alternatively, the power generation element 100 may be a battery module in which a plurality of single battery cells are connected in series or in parallel.

Yet alternatively, the power generation element 100 may be a battery pack in which a plurality of battery modules are connected in series or in parallel.

The first outer cover body 210 and the second outer cover body 220 may use a typically known outer cover material (for example, aluminum foil, aluminum alloy foil, resin film, or composite film containing aluminum and resin).

Alternatively, in a case where the power generation element 100 has a larger configuration (for example, battery module or battery pack), the material of the first outer cover body 210 and the second outer cover body 220 may use a material with higher strength (for example, metal sheet or resin sheet).

The material of the first outer cover body 210 and the second outer cover body 220 may be a material having high impermeability performance to moisture, an encapsulated gas, a gas which may be generated from the power generation element, and other substances. Since the first outer cover body 210 and the second outer cover body 220 prevent moisture from entering, for example, deterioration due to corrosion of a current collector, change in quality of a solid electrolyte, and generation of a toxic gas can be prevented from occurring.

The shape of the first outer cover body 210 and the second outer cover body 220 may be a typically known outer cover body shape (for example, lamination type, box type, or cylinder type).

The configuration (for example, shape, material, and thickness) of the first outer cover body 210 and the configuration (for example, shape, material, and thickness) of the second outer cover body 220 may be the same or may differ from one another.

In the first embodiment, the detection unit 400 detects "a gas in the first space section 310." To be more specific, the detection unit 400 may detect a detection target gas present in the first space section 310 (that is, for example, an outside atmosphere entering from the outside of the first outer cover body 210, a second gas encapsulated in the second space section 320, and a generated gas which may be generated from the power generation element 100). Further, the detection unit 400 may detect another gas, for example, a first gas encapsulated in the first space section 310 and hence being present in the first space section 310.

Also, the detection unit 400 detects a gas in the second space section 320. To be more specific, the detection unit 400 may detect a detection target gas present in the second space section 320 (that is, for example, the first gas encapsulated in the first space section 310, the outside atmosphere entering from the outside of the first outer cover body 210, and the generated gas which may be generated from the power generation element 100). Further, the detection unit 400 may detect another gas, for example, the second gas encapsulated in the second space section 320 and hence being present in the second space section 320.

It is to be noted that, in the present disclosure, expression "a detection unit detects a gas" includes that "a detection unit outputs a detection signal indicative of a detection result of a gas."

Figure 2:
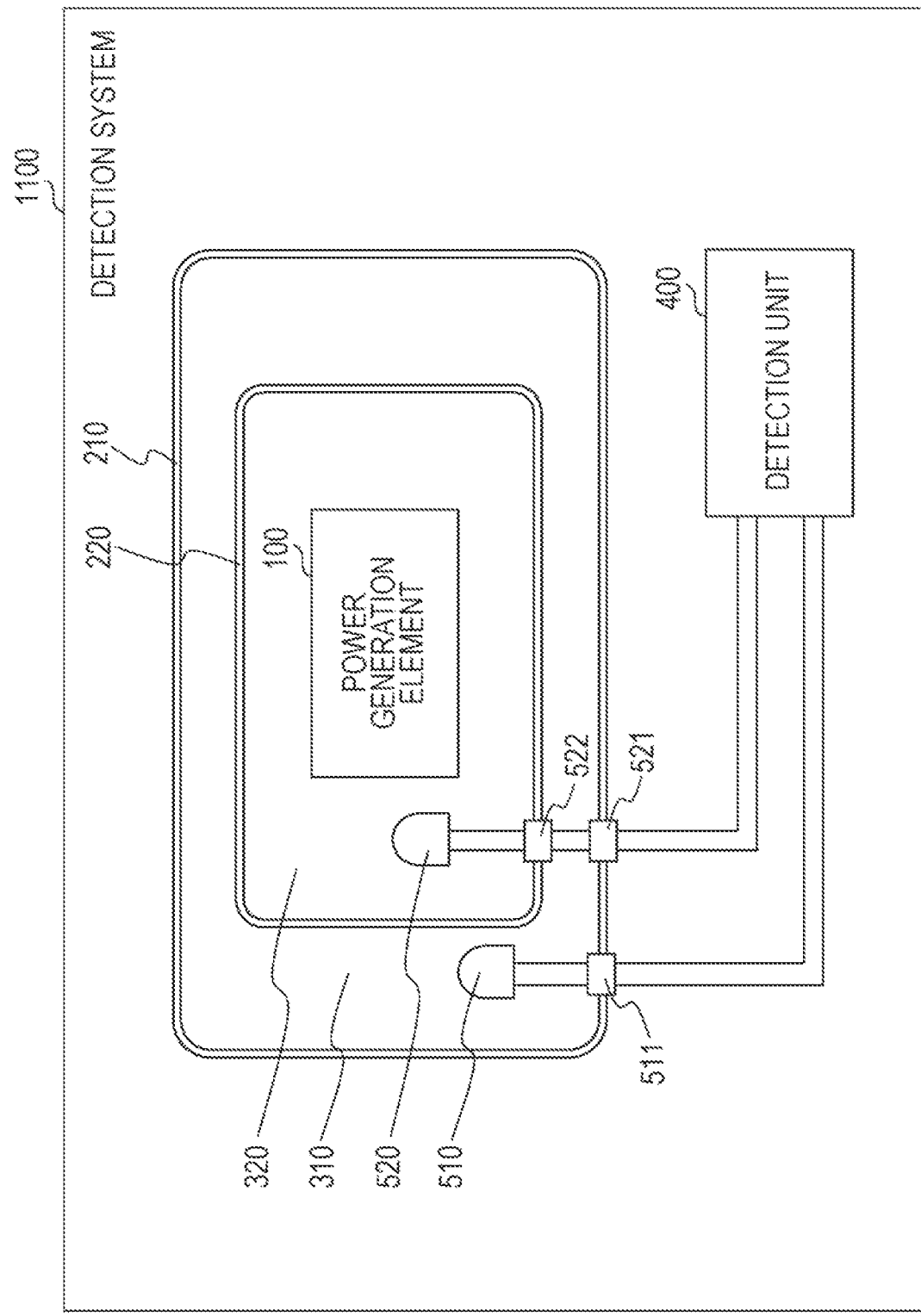
FIG. 2 illustrates a general configuration of a detection system according to the first embodiment.

FIG. 2 illustrates a general configuration of a detection system 1100 according to the first embodiment.

The detection system 1100 according to the first embodiment further includes a first sensor element 510 in addition to the configuration of the above-described detection system 1000.

The first sensor element 510 is arranged in the first space section 310.

The detection unit 400 detects the gas in the first space section 310 on the basis of a detection signal from the first sensor element 510.

With the above-described configuration, the detection system can be decreased in size as compared with a configuration (a detection system 1300, described later) including a communicating tube that causes the inside of the outer cover member to communicate with the detection unit 400.

The detection system 1100 according to the first embodiment further includes a second sensor element 520.

The second sensor element 520 is arranged in the second space section 320.

The detection unit 400 detects "the gas in the second space section 320" on the basis of a detection signal from the second sensor element 520.

The first sensor element 510 is a member that detects a detection target gas present in the first space section 310.

The second sensor element 520 is a member that detects a detection target gas present in the second space section 320.

The first sensor element 510 and the second sensor element 520 each may use a single typically known gas detection sensor (for example, constant potential electrolysis type, semiconductor type, or thermal conduction type) or a combination of two or more types.

In a case where a plurality of detection target gases are set for a sensor element, the sensor element may be an element that can detect a plurality of detection target gases. Alternatively, the sensor element may be a group of a plurality of elements that can individually respectively detect a plurality of detection target gases.

Also, as shown in FIG. 2, the first sensor element 510 may include a first connection line being a pair of connection lines connected with a sensing region of the first sensor element 510.

In the detection system 1100 according to the first embodiment, the first connection line passes through a sealing portion 511 provided at the first outer cover body 210 and extends to the outside of the first outer cover body 210.

Also, as shown in FIG. 2, the second sensor element 520 may include a second connection line being a pair of connection lines connected with a sensing region of the second sensor element 520.

In the detection system 1100 according to the first embodiment, the second connection line passes through a sealing portion 522 provided at the second outer cover body 220 and a sealing portion 521 provided at the first outer cover body 210, and extends to the outside of the first outer cover body 210.

The connection lines extending to the outside of the first outer cover body 210 are connected with the detection unit 400.

The detection unit 400 may apply a current between the pair of connection lines and may detect the voltage between the pair of connection lines. In this case, the detection unit 400 may include, for example, a current applying unit (for example, current source) and a voltage measuring unit (for example, voltmeter). The current applying unit and the voltage measuring unit may use typically known configurations.

Alternatively, the detection unit 400 may apply a voltage between the pair of connection lines and may detect the current between the pair of connection lines. In this case, the detection unit 400 may include, for example, a voltage applying unit (for example, voltage source) and a current measuring unit (for example, ammeter). The voltage applying unit and the current measuring unit may use typically known configurations.

The detection unit 400 may individually output detection signals indicative of the detection results of the gas in the first space section 310 and the gas in the second space section 320 on the basis of the magnitudes of or changes in the voltages or currents detected respectively from the first and second connection lines.

The sealing portion may use a typically known sealing material (for example, thermoplastic resin, thermosetting resin, or photo-curable resin). The material of the sealing portion may be a material having high impermeability performance to moisture, an encapsulated gas, a gas which may be generated from the power generation element 100, and other substances. Since the sealing portion prevents moisture from entering, for example, deterioration due to corrosion of a current collector, change in quality of a solid electrolyte, and generation of a toxic gas can be prevented from occurring.

Figure 3:
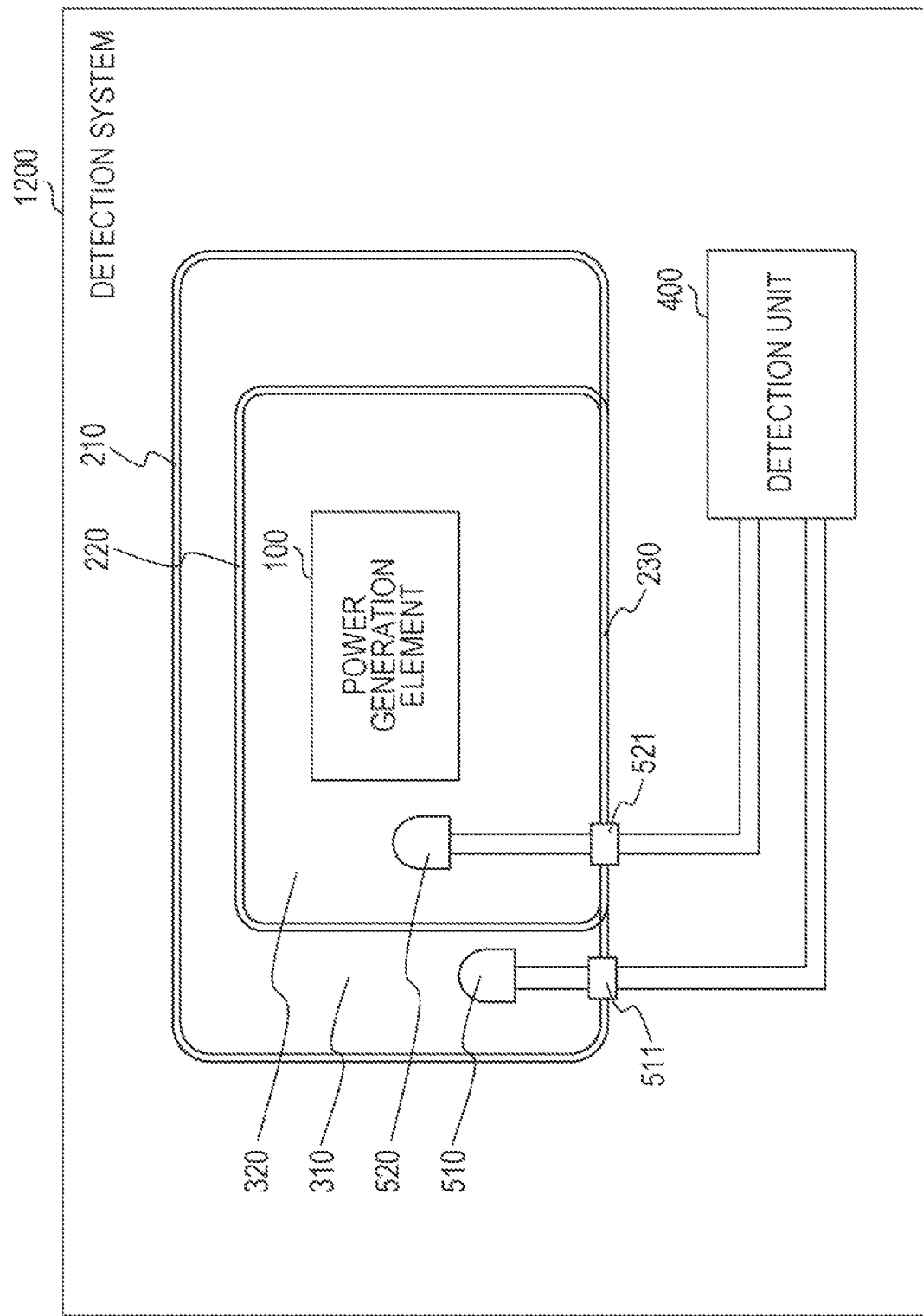
FIG. 3 illustrates a general configuration of a detection system according to the first embodiment.

FIG. 3 illustrates a general configuration of a detection system 1200 according to the first embodiment.

The detection system 1200 according to the first embodiment includes the following configuration in addition to the configuration of the above-described detection system 1100.

That is, in the detection system 1200 according to the first embodiment, a portion of the first outer cover body 210 and a portion of the second outer cover body 220 are integrated with one another and form a common outer cover portion 230.

The second connection line connected with the second sensor element 520 extends through the common outer cover portion 230 and is connected with the detection unit 400. In other words, the sealing portion 521 from which the second connection line extends is provided at the common outer cover portion 230.

With the above-described configuration, the number of sealing portions to allow the second connection line of the second sensor element 520 to extend to the outside of the outer cover member can be decreased. Accordingly, the processing step for the sealing portion can be simplified, and the processing cost of the sealing portion can be decreased. Also, a decrease in strength due to presence of a plurality of sealing portions can be prevented from occurring. Accordingly, the risk of breakage of the outer cover member can be decreased.

Figure 4:
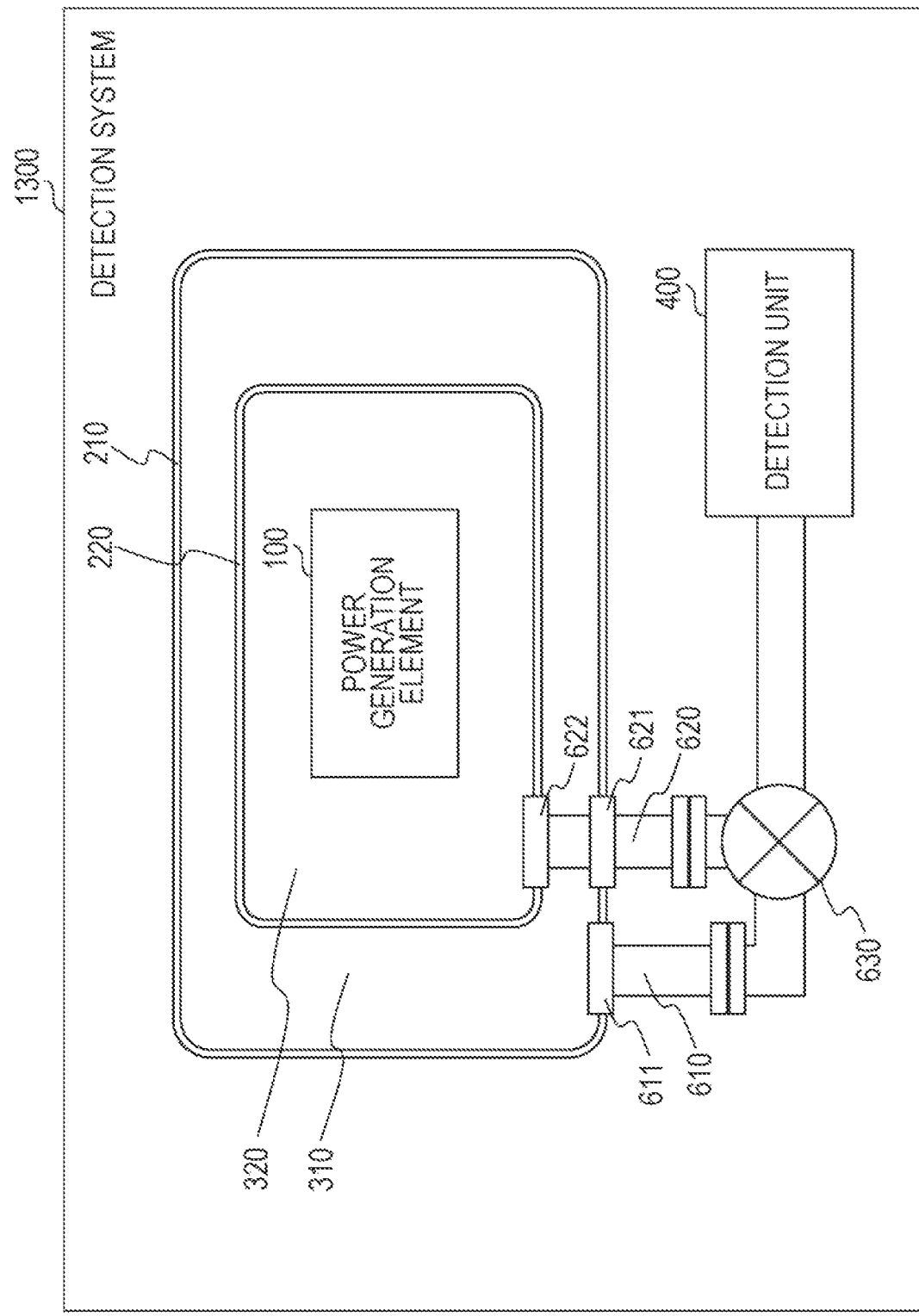
FIG. 4 illustrates a general configuration of a detection system according to the first embodiment.

FIG. 4 illustrates a general configuration of a detection system 1300 according to the first embodiment.

The detection system 1300 according to the first embodiment further includes a first communicating tube 610 in addition to the configuration of the above-described detection system 1000.

The first communicating tube 610 causes the first space section 310 to communicate with the detection unit 400.

The detection unit 400 detects "the gas in the first space section 310" introduced through the first communicating tube 610.

With the above-described configuration, a detection device or the like with higher detection sensitivity can be provided as the detection unit 400 outside the outer cover member as compared with the configuration provided with the sensor element in the outer cover member (the above-described detection system 1100). Accordingly, the detection accuracy of the breakage state of the outer cover member enveloping the power generation element 100 can be further increased.

The detection system 1300 according to the first embodiment further includes a second communicating tube 620.

The second communicating tube 620 causes the second space section 320 to communicate with the detection unit 400.

The detection unit 400 detects "the gas in the second space section 320" introduced through the second communicating tube 620.

The material of the first communicating tube 610 and the second communicating tube 620 may use a typically known communicating tube material. The material of the first communicating tube 610 and the second communicating tube 620 may be a material having high impermeability performance to moisture, an encapsulated gas, a gas which may be generated from the power generation element 100, and other substances.

Also, the first communicating tube 610 is coupled with a coupling portion 611 provided at the first outer cover body 210.

Also, the second communicating tube 620 passes through a coupling portion 621 provided at the first outer cover body 210, and is coupled with a coupling portion 622 provided at the second outer cover body 220.

The first communicating tube 610 and the second communicating tube 620 are connected with the detection unit 400.

It is to be noted that, as shown in FIG. 4, the first communicating tube 610 and the second communicating tube 620 may be connected with the detection unit 400 through an automatic switch valve 630.

The automatic switch valve 630 introduces the gas present in the first space section 310 and the gas present in the second space section 320 individually into the detection unit 400.

In the detection system 1300 according to the first embodiment, the detection unit 400 may include a gas analyzer. The gas analyzer may use a typically known gas analyzer. In this case, the gas in the first space section 310 and the gas in the second space section 320 individually introduced by the automatic switch valve 630 may be detected by the gas analyzer (for example, concentration measurement). Accordingly, the detection unit 400 may individually output detection signals indicative of the detection results of the gas in the first space section 310 and the gas in the second space section 320.

Alternatively, in the detection system 1300 according to the first embodiment, the detection unit 400 may include sensor elements corresponding to the above-described first sensor element 510 and second sensor element 520. In this case, the detection unit 400 may individually output detection signals indicative of the detection results of the gas in the first space section 310 and the gas in the second space section 320 on the basis of the magnitudes of or changes in the voltages or currents detected respectively from the sensor elements.

The coupling portion may use a typically known coupling material (for example, metal material or sealing material). The material of the coupling portion may be a material having high impermeability performance to moisture, an encapsulated gas, a gas which may be generated from the power generation element 100, and other substances.

Figure 5:
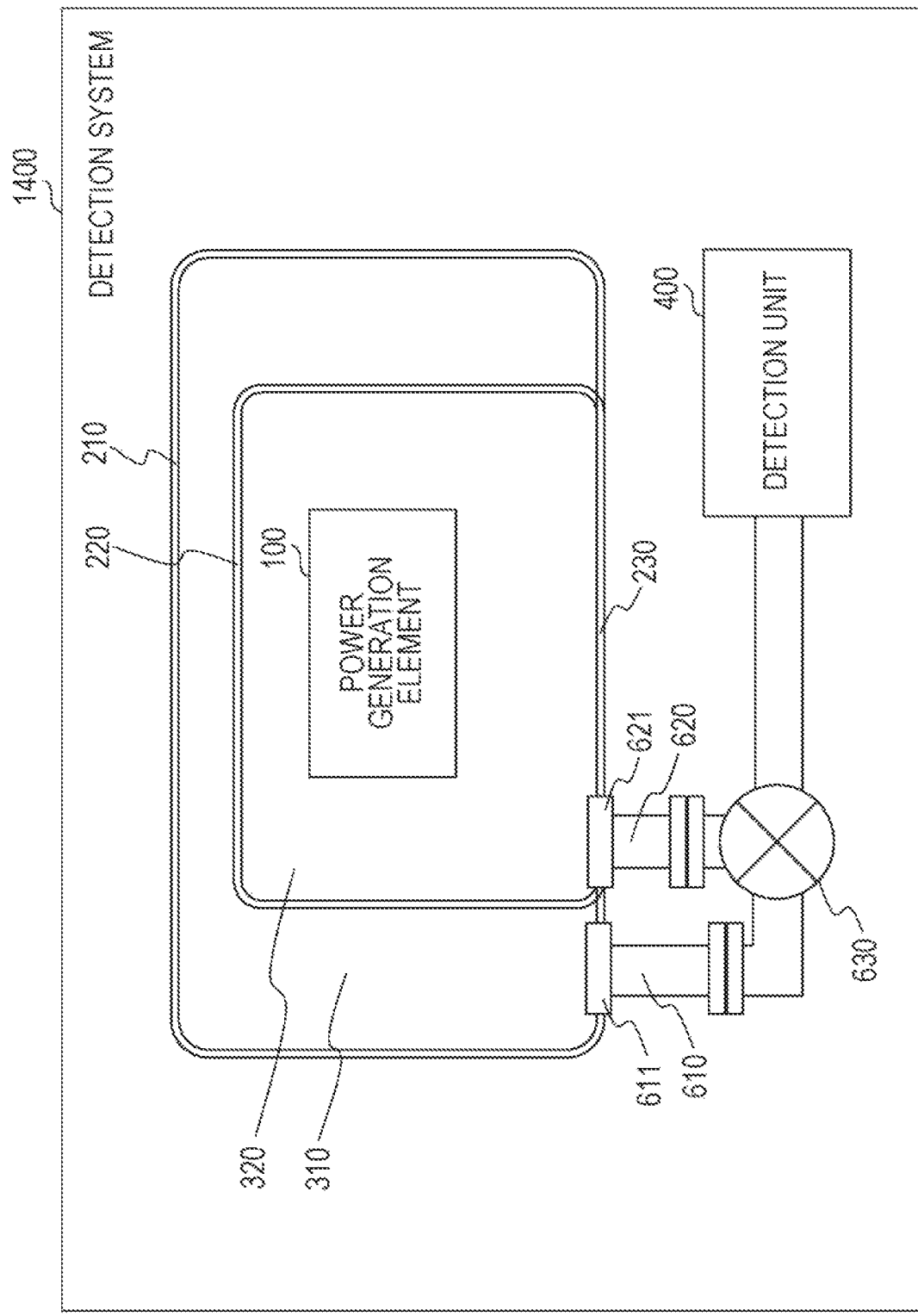
FIG. 5 illustrates a general configuration of a detection system according to the first embodiment.

FIG. 5 illustrates a general configuration of a detection system 1400 according to the first embodiment.

The detection system 1400 according to the first embodiment includes the following configuration in addition to the configuration of the above-described detection system 1300.

That is, in the detection system 1400 according to the first embodiment, a portion of the first outer cover body 210 and a portion of the second outer cover body 220 are integrated with one another and form a common outer cover portion 230.

The second communicating tube 620 is coupled with the common outer cover portion 230.

With the above-described configuration, the number of coupling portions between the second communicating tube 620 and the outer cover member can be decreased. Accordingly, the arrangement step for the coupling portion can be simplified, and the arrangement cost of the coupling portion can be decreased. Also, a decrease in strength due to presence of a plurality of coupling portions can be prevented from occurring. Accordingly, the risk of breakage of the outer cover member can be decreased.

In the detection system 1200 or the detection system 1400 according to the first embodiment, a portion of a side surface of the first outer cover body 210 and a portion of a side surface of the second outer cover body 220 may be a common member. In this case, the portion of the common member serves as the common outer cover portion 230.

Alternatively, in the detection system 1200 or the detection system 1400 according to the first embodiment, a portion of a side surface of the first outer cover body 210 and a portion of a side surface of the second outer cover body 220 may be bonded to one another in a close contact manner without a space interposed therebetween. In this case, the bonded portions serve as the common outer cover portion 230.

The respective configurations shown in aforementioned FIGS. 2 to 5 may be properly combined. For example, one of the first space section 310 and the second space section 320 may employ a detection method using a sensor element, and the other may employ a detection method using a communicating tube.

The power generation element 100 according to the first embodiment is, for example, a power generation element having charging and discharging characteristics.

Specific examples of the power generation element 100 according to the first embodiment are described below.

Figure 6:
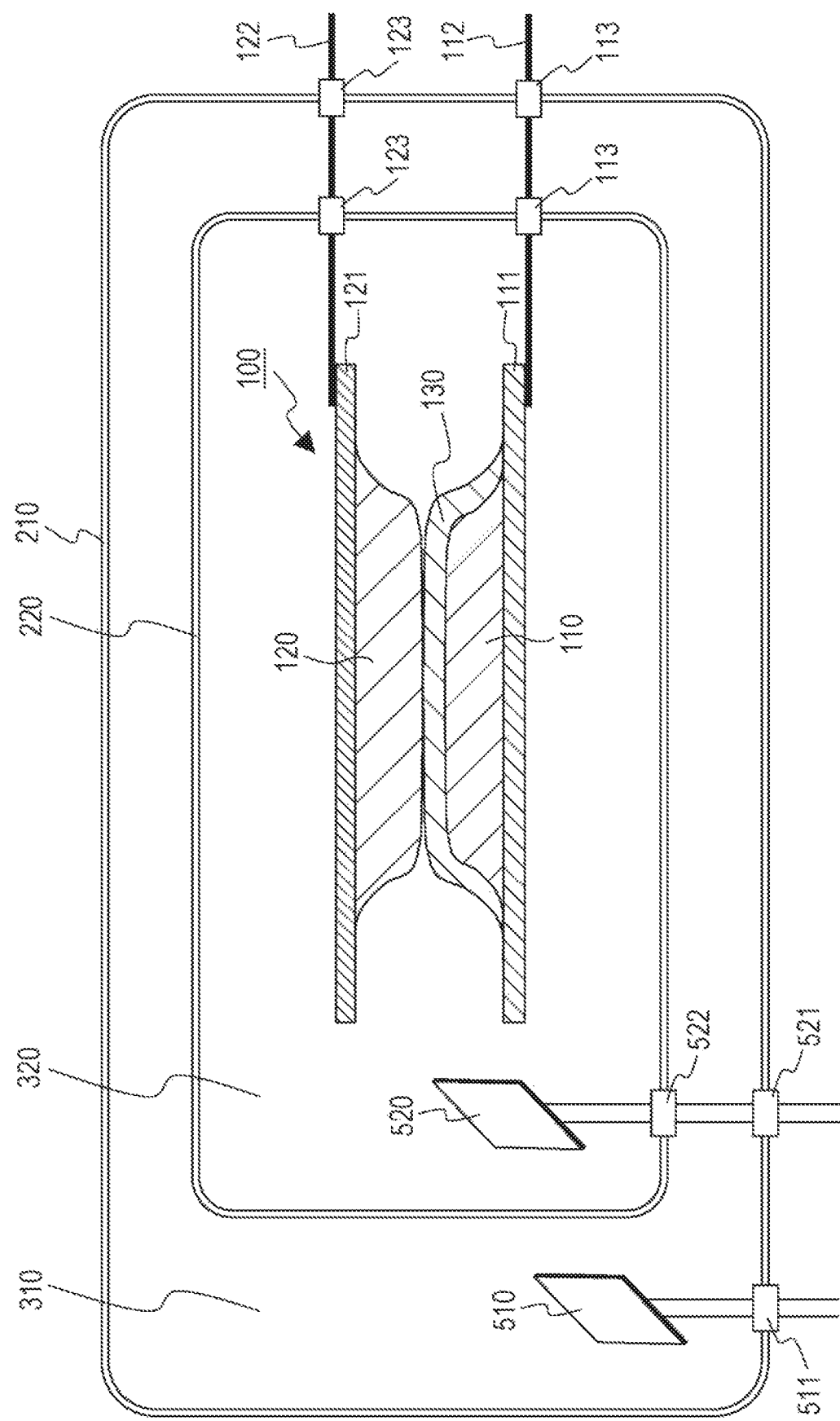
FIG. 6 illustrates a general configuration of an example of a power generation element according to the first embodiment.

FIG. 6 illustrates a general configuration of an example of the power generation element 100 according to the first embodiment.

The power generation element 100 shown in FIG. 6 includes an electrode layer 110, a first current collector 111, a counter electrode layer 120, a second current collector 121, and an electrolyte layer 130.

The electrode layer 110 is a layer containing an electrode material.

The counter electrode layer 120 is a layer being a counter electrode of the electrode layer 110. The counter electrode layer 120 is a layer containing a counter electrode material.

The first current collector 111 contacts the electrode layer 110.

The second current collector 121 contacts the counter electrode layer 120.

The electrolyte layer 130 is a layer containing an electrolyte material. For example, the electrolyte layer 130 is provided between the electrode layer 110 and the counter electrode layer 120.

In the power generation element 100, one of the electrode layer 110 and the counter electrode layer 120 is a positive electrode layer, and the other is a negative electrode layer.

For example, the electrode layer 110 may be a positive electrode layer. In this case, the electrode material is a positive electrode material. The counter electrode layer 120 is a negative electrode layer. The counter electrode material is a negative electrode material. The first current collector 111 is a positive electrode current collector. The second current collector 121 is a negative electrode current collector.

Alternatively, the electrode layer 110 may be a negative electrode layer. In this case, the electrode material is a negative electrode material. The counter electrode layer 120 is a positive electrode layer. The counter electrode material is a positive electrode material. The first current collector 111 is a negative electrode current collector. The second current collector 121 is a positive electrode current collector.

The electrolyte layer 130 may be, for example, a solid electrolyte layer. Accordingly, a battery using a solid electrolyte (all-solid lithium secondary battery) may be provided.

The positive electrode layer is, for example, a positive electrode active material layer. The positive electrode active material layer is a layer containing a positive electrode active material being a positive electrode material. The positive electrode active material contained in the positive electrode active material layer may use a known positive electrode active material (for example, lithium cobalt oxide or LiNO). The material of the positive electrode active material may use any one of various materials that allows Li to be separated from or inserted into the material.

It is to be noted that the positive electrode layer may be provided as a positive electrode mix layer obtained by adding a content material into the positive electrode active material layer. The content material of the positive electrode active material layer may use a known solid electrolyte (for example, inorganic solid electrolyte). The inorganic solid electrolyte may use, for example, a sulfide solid electrolyte or an oxide solid electrolyte. The sulfide solid electrolyte may use, for example, a mixture of $Li_2S:P_2S_5$. The surface of the positive electrode active material may be coated with a solid electrolyte. Also, the content material of the positive electrode active material layer may use a conductive material (for example, acetylene black), a binder (for example, polyvinylidene fluoride), and another material.

The positive electrode layer may be fabricated by applying a coating paste, obtained by mixing and kneading the positive electrode active material, the content material, and a solvent, on a surface of the positive electrode current collector and drying the coating paste. To increase the density of the positive electrode layer, the positive electrode layer may be pressed after drying. The thickness of the positive electrode layer fabricated in this way is, for example, 5 to 300 μm.

The negative electrode layer is, for example, a negative electrode active material layer. The negative electrode active material layer is a layer containing a negative electrode active material being a negative electrode material. The negative electrode active material contained in the negative electrode active material layer may use a known negative electrode active material (for example, graphite). The material of the negative electrode active material may use any one of various materials that allows Li to be separated from or inserted into the material.

It is to be noted that the negative electrode layer may be provided as a negative electrode mix layer obtained by adding a content material into the negative electrode active material layer. The content material of the negative electrode active material layer may use a known solid electrolyte (for example, inorganic solid electrolyte). The inorganic solid electrolyte may use, for example, a sulfide solid electrolyte or an oxide solid electrolyte. The sulfide solid electrolyte may use, for example, a mixture of $Li_2S:P_2S_5$. Also, the content material of the negative electrode active material layer may use a conductive material (for example, acetylene black), a binder (for example, polyvinylidene fluoride), and another material.

The negative electrode layer may be fabricated by applying a coating paste, obtained by mixing and kneading the negative electrode active material, the content material, and a solvent, on a surface of the negative electrode current collector and drying the coating paste. To increase the density of the negative electrode layer, the negative electrode layer may be pressed after drying. The thickness of the negative electrode layer fabricated in this way is, for example, from 5 to 300 μm.

Also, in the power generation element 100, the formation range of the negative electrode active material layer may be larger than the formation range of the positive electrode active material layer. Accordingly, a defect of a battery (for example, decrease in reliability) due to, for example, precipitation of lithium is possibly prevented from occurring.

Alternatively, in the power generation element 100, the formation ranges of the positive electrode active material layer and the negative electrode active material layer may be the same.

The solid electrolyte layer is a layer containing a solid electrolyte. For example, the solid electrolyte layer is provided between the positive electrode layer and the negative electrode layer.

The solid electrolyte contained in the solid electrolyte layer may use a known solid electrolyte (for example, inorganic solid electrolyte). The inorganic solid electrolyte may use, for example, a sulfide solid electrolyte or an oxide solid electrolyte. The sulfide solid electrolyte may use, for example, a mixture of $Li_2S:P_2S_5$. The sulfide solid electrolyte has high ion conductivity and high flexibility.

Also, the content material of the solid electrolyte layer may use a binder (for example, polyvinylidene fluoride) and another material.

The solid electrolyte layer may be fabricated by applying a coating paste, obtained by mixing and kneading the solid electrolyte, the content material, and a solvent, on the positive electrode active material layer or the negative electrode active material layer, and drying the coating paste. A multilayer body including the positive electrode current collector, the positive electrode layer, the solid electrolyte layer, the negative electrode layer, and the negative electrode current collector is pressed, and hence the power generation element may be fabricated. By pressing, the respective layers can be brought into a mutually dense joint state. At joining, the position in the formation plane of the positive electrode layer may not protrude from the position in the formation pane of the negative electrode layer.

Also, in the power generation element 100, the positive electrode layer and the negative electrode layer may be formed in a narrower range than those of the positive electrode current collector and the negative electrode current collector. In this case, the solid electrolyte layer may be formed in a larger area than that of any one of the positive electrode active material layer and the negative electrode active material layer. Accordingly, a short circuit due to direct contact between the positive electrode layer and the negative electrode layer can be prevented from being made.

Also, in the power generation element 100, the solid electrolyte layer may be formed in the same range as that of the positive electrode current collector or the negative electrode current collector.

Alternatively, in the power generation element 100, the solid electrolyte layer may be formed in a narrower range than that of the positive electrode current collector or the negative electrode current collector.

The positive electrode current collector may use metal foil or another material foil (for example, SUS foil or Al foil). The thickness of the positive electrode current collector may be, for example, 5 to 100 μm.

The negative electrode current collector may use metal foil or another material foil (for example, SUS foil or Cu foil). The thickness of the negative electrode current collector may be, for example, 5 to 100 μm.

It is to be noted that the order of formation of the respective layers in the power generation element 100 in the manufacturing step is not particularly limited. Also, the forming method of the respective layers in the power generation element 100 may use, for example, sequential stacking, bonding, transferring, or a combination method of these processes.

It is to be noted that the detection system according to the first embodiment may further include a first lead wire 112 and a second lead wire 122 as shown in FIG. 6.

A first end of the first lead wire 112 is connected with the first current collector 111. Also, a second end of the first lead wire 112 extends to the outside of the first outer cover body 210 and the second outer cover body 220. In this case, the gap between the first lead wire 112 and the first outer cover body 210 and the gap between the first lead wire 112 and the second outer cover body 220 each may be sealed with a sealing portion 113.

A first end of the second lead wire 122 is connected with a current collector being a counter electrode for the first current collector 111 (for example, the second current collector 121 in FIG. 6). Also, a second end of the second lead wire 122 extends to the outside of the first outer cover body 210 and the second outer cover body 220. In this case, the gap between the second lead wire 122 and the first outer cover body 210 and the gap between the second lead wire 122 and the second outer cover body 220 each may be sealed with a sealing portion 123.

The first lead wire 112 and the second lead wire 122 may be connected with a load to which electric power is supplied from the power generation element 100 or a charging device that charges the power generation element 100 with electric power.

It is to be noted that, in the first embodiment, at least one of the electrode layer 110, the counter electrode layer 120, and the electrolyte layer 130 may contain a sulfur-based material. The sulfur-based material is, for example, a material that generates hydrogen sulfide ($H_2S$) gas when reacting with moisture. The sulfur-based material may be, for example, the above-described sulfide solid electrolyte.

It is to be noted that, in the first embodiment, the first sensor element 510 and the second sensor element 520 may be thin-film sensors as shown in FIG. 6. Accordingly, the sealing structures of the first sensor element 510 and the second sensor element 520 can be simplified. Also, the occupying volumes of the first sensor element 510 and the second sensor element 520 can be decreased.

Figure 7:
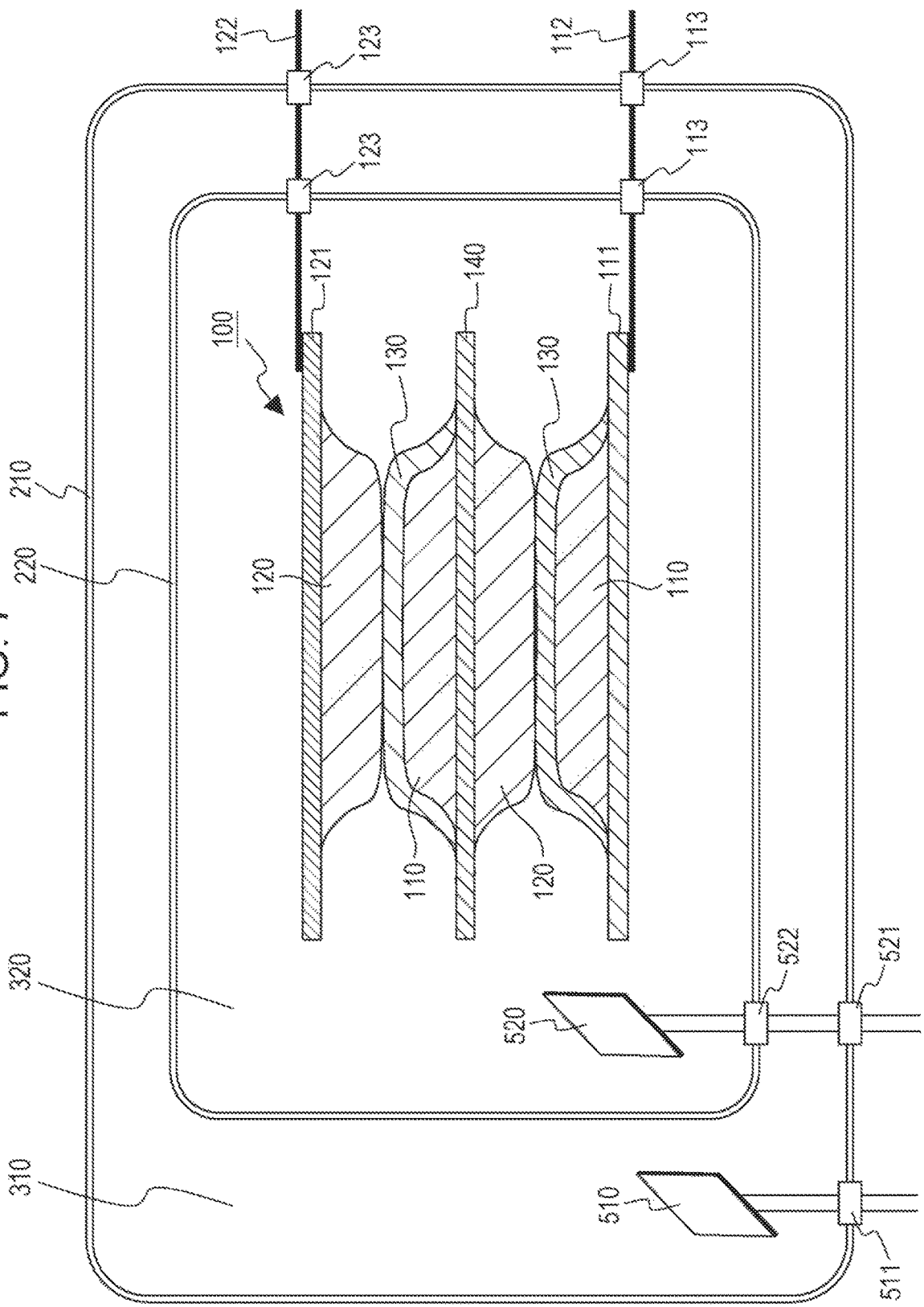
FIG. 7 illustrates a general configuration of another example of the power generation element according to the first embodiment.

FIG. 7 illustrates a general configuration of another example of the power generation element 100 according to the first embodiment;

A power generation element 100 shown in FIG. 7 has a configuration in which two single batteries shown in FIG. 6 are stacked.

A bipolar current collector 140 shown in FIG. 7 is a bipolar current collector having a positive electrode layer and a negative electrode layer formed on its upper and lower surfaces. The bipolar current collector may be a single member. Alternatively, the bipolar current collector may have a configuration in which members of two or more layers are integrated with one another by bonding, joining, or stacking.

As described above, the power generation element 100 according to the first embodiment may be configured as a bipolar battery in which a plurality of single batteries are connected in series.

A bipolar battery (bipolar all-solid battery) may be fabricated by repetitively stacking bipolar current collectors, each of which has a positive electrode layer and a negative electrode layer formed on its front and back surfaces, with a solid electrolyte layer interposed therebetween. In this case, a plurality of power generation elements may be pressed. Accordingly, the series arrangement and connection state of the respective power generation elements can become more stable.

A bipolar battery in which a plurality of single batteries are connected in series can provide, for example, high voltage.

The number of stack of single batteries according to the first embodiment may be two or more (for example, 2 to 200). By adjusting the number of stack of power generation elements, the output can be adjusted in accordance with the purpose of use of batteries (electronic device, electrical equipment, electrical vehicle, stationary battery, or another purpose).

Second Embodiment

A second embodiment is described below. The redundant description provided in the above-described first embodiment is properly omitted.

Figure 8:
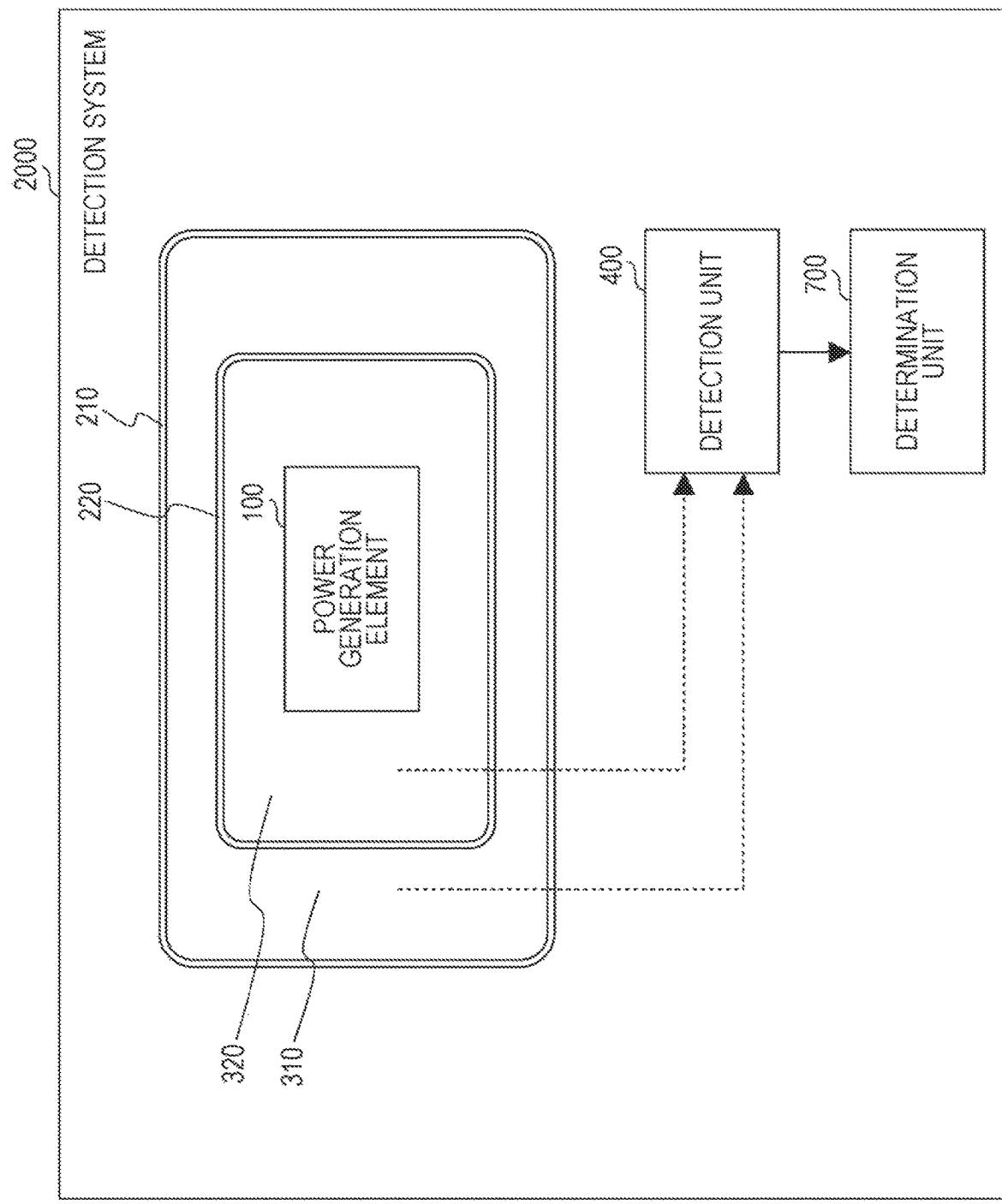
FIG. 8 illustrates a general configuration of a detection system according to a second embodiment.

FIG. 8 illustrates a general configuration of a detection system 2000 according to the second embodiment.

The detection system 2000 according to the second embodiment includes the following configuration in addition to the configuration of the detection system according to the above-described first embodiment.

That is, in the detection system 2000 according to the second embodiment, a first gas is encapsulated in the first space section 310.

The detection unit 400 detects an outside atmosphere entering from the outside of the first outer cover body 210, in the first space section 310.

The detection unit 400 detects the first gas in the second space section 320.

With the above-described configuration, the detection accuracy of the breakage state of the outer cover member enveloping the power generation element 100 can be further increased. To be specific, the presence of breakage of the first outer cover body 210 and the second outer cover body 220 can be detected on the basis of the detection result of the outside atmosphere in the first space section 310 and the detection result of the first gas in the second space section 320. Accordingly, the generation of breakage of the first outer cover body 210 and the second outer cover body 220 can be detected with higher accuracy at an earlier stage.

The first gas may use, for example, a rare gas (helium, neon, argon, or another gas) or nitrogen. The first gas is, for example, an inert gas for the power generation element 100 and the outer cover member.

The outside atmosphere may be, for example, the atmosphere (the air). Alternatively, if a certain kind of encapsulated gas is present outside the first outer cover body 210, the outside atmosphere may be the encapsulated gas.

Also, the detection system 2000 according to the second embodiment further includes a determination unit 700.

The determination unit 700 determines the breakage states of the first outer cover body 210 and the second outer cover body 220 on the basis of the detection result (for example, a detection signal) of the detection unit 400.

In the detection system 2000 according to the second embodiment, the detection unit 400 outputs the detection result (for example, the detection signal) to the determination unit 700.

FIGS. 9A to 9D each illustrate the breakage states of the first outer cover body 210 and the second outer cover body 220.

Figure 9A:
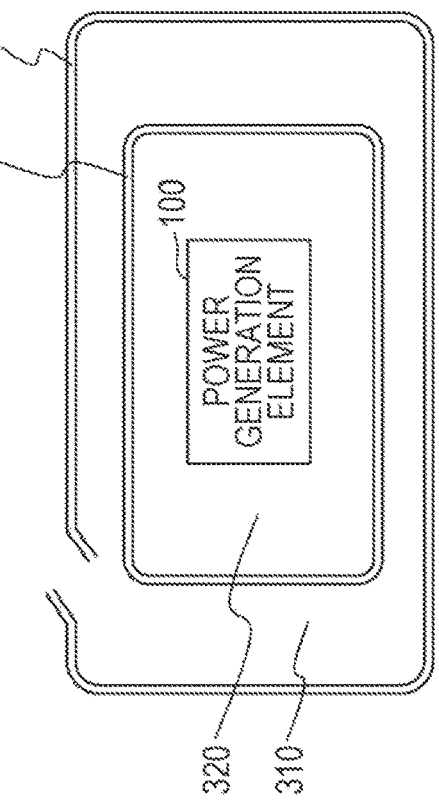
FIGS. 9A to 9D each illustrate the breakage states of a first outer cover body and a second outer cover body.

FIG. 9A shows a state in which neither the first outer cover body 210 nor the second outer cover body 220 is broken (case A).

Figure 9B:
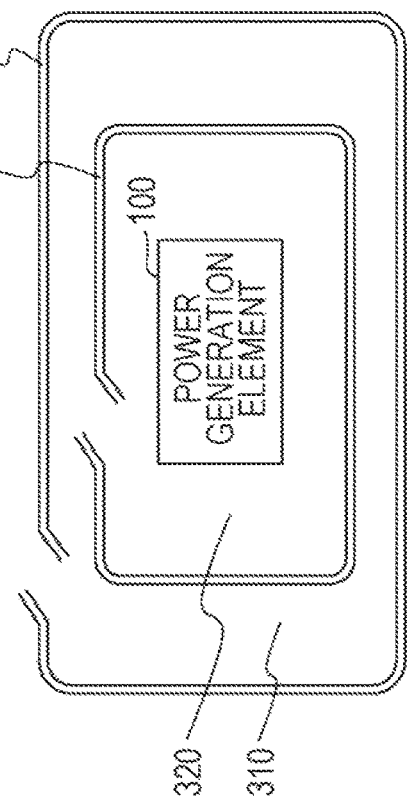

FIG. 9B shows a state in which the first outer cover body 210 is broken, and the second outer cover body 220 is not broken (case B).

Figure 9C:
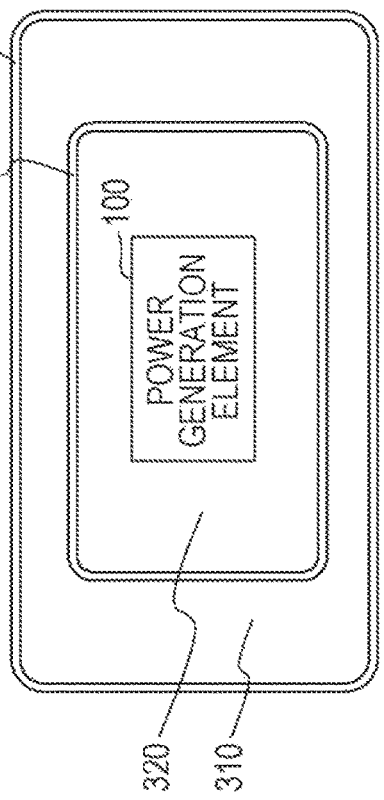

FIG. 9C shows a state in which the first outer cover body 210 is not broken, and the second outer cover body 220 is broken (case C).

Figure 9D:
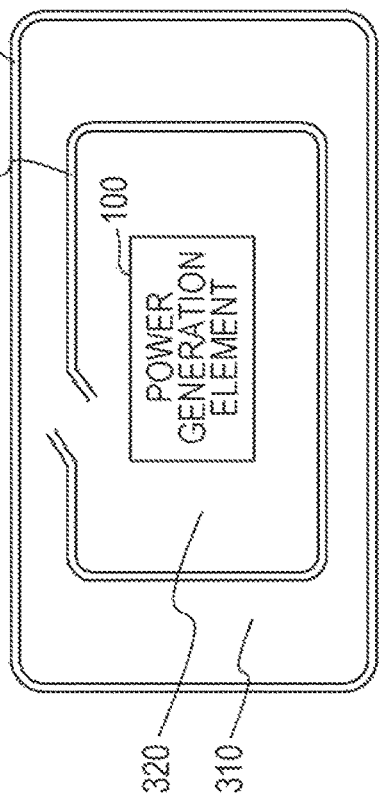

FIG. 9D shows a state in which both the first outer cover body 210 and the second outer cover body 220 are broken (case D).

It is to be noted that, in the present disclosure, expression "an outer cover body is broken" represents that "a portion through which a gas can pass is generated at a portion of an outer cover body." For example, expression "an outer cover body is broken" may represent that "an aperture (or opening) or a crack is generated at a portion of an outer cover body." Such an opening (or aperture) and a crack may be generated due to an impact from the outside, or deterioration or corrosion of an outer cover body.

If the first outer cover body 210 is broken, the gas present outside the first outer cover body 210 flows to the inside of the first outer cover body 210 (that is, the first space section 310) through the first outer cover body 210. Also, the gas present inside the first outer cover body 210 (that is, the first space section 310) flows to the outside of the first outer cover body 210 through the first outer cover body 210.

Also, if the second outer cover body 220 is broken, the gas present outside the second outer cover body 220 (that is, the first space section 310) flows to the inside of the second outer cover body 220 (that is, the second space section 320) through the second outer cover body 220. Also, the gas present inside the second outer cover body 220 (that is, the second space section 320) flows to the outside of the second outer cover body 220 (that is, the first space section 310) through the second outer cover body 220.

FIG. 10 illustrates a determination method of the determination unit 700 according to the second embodiment.

In the detection system 2000 according to the second embodiment, the determination unit 700 may execute the determination method shown in FIG. 10.

That is, if the detection result of the detection unit 400 indicates a state in which the outside atmosphere is not detected in the first space section 310 and the first gas is not detected in the second space section 320, the determination unit 700 determines that neither the first outer cover body 210 nor the second outer cover body 220 is broken (case A-10).

Also, if the detection result of the detection unit 400 indicates a state in which the outside atmosphere is detected in the first space section 310 and the first gas is not detected in the second space section 320, the determination unit 700 determines that the first outer cover body 210 is broken and the second outer cover body 220 is not broken (case B-10).

Also, if the detection result of the detection unit 400 indicates a state in which the outside atmosphere is not detected in the first space section 310 and the first gas is detected in the second space section 320, the determination unit 700 determines that the first outer cover body 210 is not broken and the second outer cover body 220 is broken (case C-10).

Also, if the detection result of the detection unit 400 indicates a state in which the outside atmosphere is detected in the first space section 310 and the first gas is detected in the second space section 320, the determination unit 700 determines that both the first outer cover body 210 and the second outer cover body 220 are broken (case D-10).

With the above-described configuration, the determination accuracy of the breakage state of the outer cover member enveloping the power generation element 100 can be increased. To be specific, the presence of breakage of the first outer cover body 210 and the second outer cover body 220 can be individually determined on the basis of the detection result of the outside atmosphere in the first space section 310 and the detection result of the first gas in the second space section 320. Accordingly, the generation of breakage of the first outer cover body 210 and the second outer cover body 220 can be determined with high accuracy at an early stage.

It is to be noted that, in the detection system 2000 according to the second embodiment, a second gas may be encapsulated in the second space section 320. The second gas is a gas different from the first gas.

In this case, the detection unit 400 may detect the outside atmosphere and the second gas, in the first space section 310.

With the above-described configuration, the detection accuracy of the breakage state of the outer cover member enveloping the power generation element 100 can be further increased. To be specific, the presence of breakage of the first outer cover body 210 and the second outer cover body 220 can be detected on the basis of the detection results of the outside atmosphere and the second gas in the first space section 310 and the detection result of the first gas in the second space section 320. That is, by individually detecting not only the first gas but also the second gas, the presence of breakage of the second outer cover body 220 can be detected even if one of the first gas and the second gas is erroneously detected or if it is difficult to detect one of the first gas and the second gas. Accordingly, the generation of breakage of the first outer cover body 210 and the second outer cover body 220 can be detected with higher accuracy at an earlier stage.

The second gas may use, for example, a rare gas (helium, neon, argon, or another gas) or nitrogen. The second gas is, for example, an inert gas for the power generation element 100 and the outer cover member.

The first gas and the second gas may be gases of kinds or components different from one another. Further, the first gas and the second gas may be gases of kinds or components different from the outside atmosphere. Accordingly, the detection accuracy of the breakage state of the outer cover member enveloping the power generation element 100 can be further increased.

It is to be noted that the first gas, the second gas, and the outside atmosphere may be gases mutually having the same component (substance) with different concentrations.

FIG. 11 illustrates a determination method of the determination unit 700 according to the second embodiment.

In the detection system 2000 according to the second embodiment, the determination unit 700 may execute the determination method shown in FIG. 11.

That is, if the detection result of the detection unit 400 indicates a state in which the outside atmosphere is not detected in the first space section 310, the second gas is not detected in the first space section 310, and the first gas is not detected in the second space section 320, the determination unit 700 determines that neither the first outer cover body 210 nor the second outer cover body 220 is broken (case A-20).

Also, if the detection result of the detection unit 400 indicates a state in which the outside atmosphere is detected in the first space section 310, the second gas is not detected in the first space section 310, and the first gas is not detected in the second space section 320, the determination unit 700 determines that the first outer cover body 210 is broken and the second outer cover body 220 is not broken (case B-20).

Also, if the detection result of the detection unit 400 indicates a state in which the outside atmosphere is not detected in the first space section 310, the second gas is detected in the first space section 310, and the first gas is detected in the second space section 320, the determination unit 700 determines that the first outer cover body 210 is not broken and the second outer cover body 220 is broken (case C-20).

Also, if the detection result of the detection unit 400 indicates a state in which the outside atmosphere is detected in the first space section 310, the second gas is detected in the first space section 310, and the first gas is detected in the second space section 320, the determination unit 700 determines that both the first outer cover body 210 and the second outer cover body 220 are broken (case D-20).

With the above-described configuration, the determination accuracy of the breakage state of the outer cover member enveloping the power generation element 100 can be further increased. To be specific, the presence of breakage of the first outer cover body 210 and the second outer cover body 220 can be individually determined on the basis of the detection results of the outside atmosphere and the second gas in the first space section 310 and the detection result of the first gas in the second space section 320. That is, by using the detection result in which the detection of the first gas matches the detection of the second gas for determination, the presence of breakage of the second outer cover body 220 can be correctly determined even if one of the first gas and the second gas is erroneously detected. Accordingly, the generation of breakage of the first outer cover body 210 and the second outer cover body 220 can be determined with higher accuracy at an earlier stage.

It is to be noted that, in the detection system 2000 according to the second embodiment, the determination unit 700 may further execute the following determination method.

That is, if the detection result of the detection unit 400 indicates a state in which the outside atmosphere is not detected in the first space section 310, and the second gas is detected in the first space section 310 and/or the first gas is detected in the second space section 320, the determination unit 700 determines that the first outer cover body 210 is not broken and the second outer cover body 220 is broken (case C-20, case C-21, or case C-22).

Also, if the detection result of the detection unit 400 indicates a state in which the outside atmosphere is detected in the first space section 310, and the second gas is detected in the first space section 310 and/or the first gas is detected in the second space section 320, the determination unit 700 determines that both the first outer cover body 210 and the second outer cover body 220 are broken (case D-20, case D-21, or case D-22).

With the above-described configuration, the determination accuracy of the breakage state of the outer cover member enveloping the power generation element 100 can be further increased. To be specific, the presence of breakage of the first outer cover body 210 and the second outer cover body 220 can be individually determined on the basis of the detection results of the outside atmosphere and the second gas in the first space section 310 and the detection result of the first gas in the second space section 320. That is, by using the detection result in the case where at least one of the first gas and the second gas is detected for determination, the presence of breakage of the second outer cover body 220 can be determined even if it is difficult to detect one of the first gas and the second gas (for example, if a failure of the detection unit 400 occurs or if the first gas or the second gas is lost). To be more specific, a case is conceivable in which the amounts and speeds of the outside atmosphere, the first gas, and the second gas flowing into another space section or flowing out from another space section when each outer cover body is broken in accordance with the broken portion (upper portion or lower portion) of each outer cover body and differences in specific gravities of the outside atmosphere, the first gas, and the second gas. In this case, even if any one of the first gas and the second gas cannot sufficiently flow in or flow out through the broken portion of each outer cover body, the presence of breakage of the second outer cover body 220 can be determined. Accordingly, the generation of breakage of the first outer cover body 210 and the second outer cover body 220 can be determined at an earlier stage.

In the detection system 2000 according to the second embodiment, the detection unit 400 may detect the first gas and the outside atmosphere in the second space section 320.

With the above-described configuration, the detection accuracy of the breakage state of the outer cover member enveloping the power generation element 100 can be further increased. To be specific, the presence of breakage of the first outer cover body 210 and the second outer cover body 220 can be detected on the basis of the detection results of the outside atmosphere and the second gas in the first space section 310 and the detection results of the first gas and the outside atmosphere in the second space section 320. That is, by also detecting the outside atmosphere in the second space section 320, the presence of breakage of the second outer cover body 220 can be correctly detected even if one of the first gas and the second gas is erroneously detected or if it is difficult to detect one of the first gas and the second gas. Accordingly, the generation of breakage of the first outer cover body 210 and the second outer cover body 220 can be detected with higher accuracy at an earlier stage.

FIG. 12 illustrates a determination method of the determination unit 700 according to the second embodiment.

In the detection system 2000 according to the second embodiment, the determination unit 700 may execute the determination method shown in FIG. 11.

That is, if the detection result of the detection unit 400 indicates a state in which the outside atmosphere is not detected in the first space section 310, the second gas is not detected in the first space section 310, the first gas is not detected in the second space section 320, and the outside atmosphere is not detected in the second space section 320, the determination unit 700 determines that neither the first outer cover body 210 nor the second outer cover body 220 is broken (case A-30).

Also, if the detection result of the detection unit 400 indicates a state in which the outside atmosphere is detected in the first space section 310, the second gas is not detected in the first space section 310, the first gas is not detected in the second space section 320, and the outside atmosphere is not detected in the second space section 320, the determination unit 700 determines that the first outer cover body 210 is broken and the second outer cover body 220 is not broken (case B-30).

Also, if the detection result of the detection unit 400 indicates a state in which the outside atmosphere is not detected in the first space section 310, the second gas is detected in the first space section 310, the first gas is detected in the second space section 320, and the outside atmosphere is not detected in the second space section 320, the determination unit 700 determines that the first outer cover body 210 is not broken and the second outer cover body 220 is broken (case C-30).

Also, if the detection result of the detection unit 400 indicates a state in which the outside atmosphere is detected in the first space section 310, the second gas is detected in the first space section 310, the first gas is detected in the second space section 320, and the outside atmosphere is detected in the second space section 320, the determination unit 700 determines that both the first outer cover body 210 and the second outer cover body 220 are broken (case D-30).

With the above-described configuration, the determination accuracy of the breakage state of the outer cover member enveloping the power generation element 100 can be further increased. To be specific, the presence of breakage of the first outer cover body 210 and the second outer cover body 220 can be individually determined on the basis of the detection results of the outside atmosphere and the second gas in the first space section 310 and the detection results of the first gas and the outside atmosphere in the second space section 320. That is, by also using the detection result of the outside atmosphere in the second space section 320, the presence of breakage of the second outer cover body 220 can be correctly determined even if one of the first gas and the second gas is erroneously detected. Accordingly, the generation of breakage of the first outer cover body 210 and the second outer cover body 220 can be determined with higher accuracy at an earlier stage.

It is to be noted that, in the detection system 2000 according to the second embodiment, the determination unit 700 may further execute the following determination method.

That is, if the detection result of the detection unit 400 indicates a state in which the outside atmosphere is detected in the first space section 310 and the outside atmosphere is detected in the second space section 320, the determination unit 700 determines that both the first outer cover body 210 and the second outer cover body 220 are broken (case D-30, case D-31, case D-32, or case D-33).

With the above-described configuration, the determination accuracy of the breakage state of the outer cover member enveloping the power generation element 100 can be further increased. To be specific, the presence of breakage of the first outer cover body 210 and the second outer cover body 220 can be individually determined on the basis of the detection results of the outside atmosphere and the second gas in the first space section 310 and the detection results of the first gas and the outside atmosphere in the second space section 320. That is, by using at least the detection result in the case where the outside atmosphere is detected in the second space section 320, the presence of breakage of the first outer cover body 210 and the second outer cover body 220 can be determined even if it is difficult to detect one of the first gas and the second gas (for example, if a failure of the detection unit 400 occurs or if the first gas or the second gas is lost). To be more specific, a case is conceivable in which the amounts and speeds of the outside atmosphere, the first gas, and the second gas flowing into another space section or flowing out from another space section when each outer cover body is broken in accordance with the broken portion (upper portion or lower portion) of each outer cover body and differences in specific gravities of the outside atmosphere, the first gas, and the second gas. In this case, even if any one of the first gas and the second gas cannot sufficiently flow in or flow out through the broken portion of each outer cover body, the presence of breakage of the second outer cover body 220 can be determined. Accordingly, the generation of breakage of the first outer cover body 210 and the second outer cover body 220 can be determined at an earlier stage.

It is to be noted that, in the detection system 2000 according to the second embodiment, the power generation element 100 may contain a material which contributes to generation of a generated gas.

In this case, the detection unit 400 may detect the generated gas in the first space section 310 and the generated gas in the second space section 320.

With the above-described configuration, the detection accuracy of the breakage state of the outer cover member enveloping the power generation element 100 can be increased. To be specific, the presence of breakage of the second outer cover body 220 can be detected on the basis of the detection result of the generated gas which may be generated in the second space section 320. Accordingly, the generation of breakage of the second outer cover body 220 can be detected with higher accuracy at an earlier stage. Hence, for example, if the second outer cover body 220 is broken, a measure of stopping use of the power generation element 100 or another measure can be executed at an early stage. Accordingly, in particular, even if the generated gas is a toxic gas (for example, hydrogen sulfide gas), the safety of the system using the power generation element 100 can be maintained.

The material which contributes to generation of the generated gas may be, for example, the above-described sulfur-based material (for example, sulfide solid electrolyte). In this case, the generated gas is hydrogen sulfide gas.

It is to be noted that, in the detection system 2000 according to the second embodiment, the determination unit 700 may further execute the following determination method.

That is, if the detection result of the detection unit 400 indicates a state in which the generated gas is not detected in the first space section 310 and the generated gas is detected in the second space section 320, the determination unit 700 determines that the second outer cover body 220 is not broken.

Also, if the detection result of the detection unit 400 indicates a state in which the generated gas is detected in the first space section 310 and the generated gas is detected in the second space section 320, the determination unit 700 determines that the second outer cover body 220 is broken.

With the above-described configuration, the determination accuracy of the breakage state of the outer cover member enveloping the power generation element 100 can be further increased. To be specific, the presence of breakage of the second outer cover body 220 can be determined on the basis of the detection results of the generated gas in the first space section 310 and the second space section 320. Accordingly, the generation of breakage of the second outer cover body 220 can be determined with higher accuracy at an earlier stage.

It is to be noted that the determination method based on the detection result of the generated gas may be executed in combination with at least one of the determination methods illustrated in aforementioned FIGS. 10 to 12.

In this case, if the determination result of the determination method based on the detection result of the generated gas differs from the determination result of the at least one of the determination methods illustrated in aforementioned FIGS. 10 to 12, the determination result of the determination method based on the detection result of the generated gas may have priority (may be employed). Accordingly, even if the generated gas continuously issues to the outside of the outer cover member and hence the outside atmosphere cannot flow to the inside of the outer cover member, since the determination is based on the detection result of the generated gas, the determination accuracy of the breakage state of the outer cover member can be further increased.

Alternatively, if the determination result of the determination method based on the detection result of the generated gas differs from the determination result of the at least one of the determination methods illustrated in aforementioned FIGS. 10 to 12, the determination result of the at least one of the determination methods illustrated in aforementioned FIGS. 10 to 12 may have priority (may be employed). Accordingly, even if the generation amount of the generated gas is very small and hence the generated gas cannot sufficiently flow into the first space section 310, since the determination is based on the detection result of a gas other than the generated gas, the determination accuracy of the breakage state of the outer cover member can be further increased.

Figure 13:
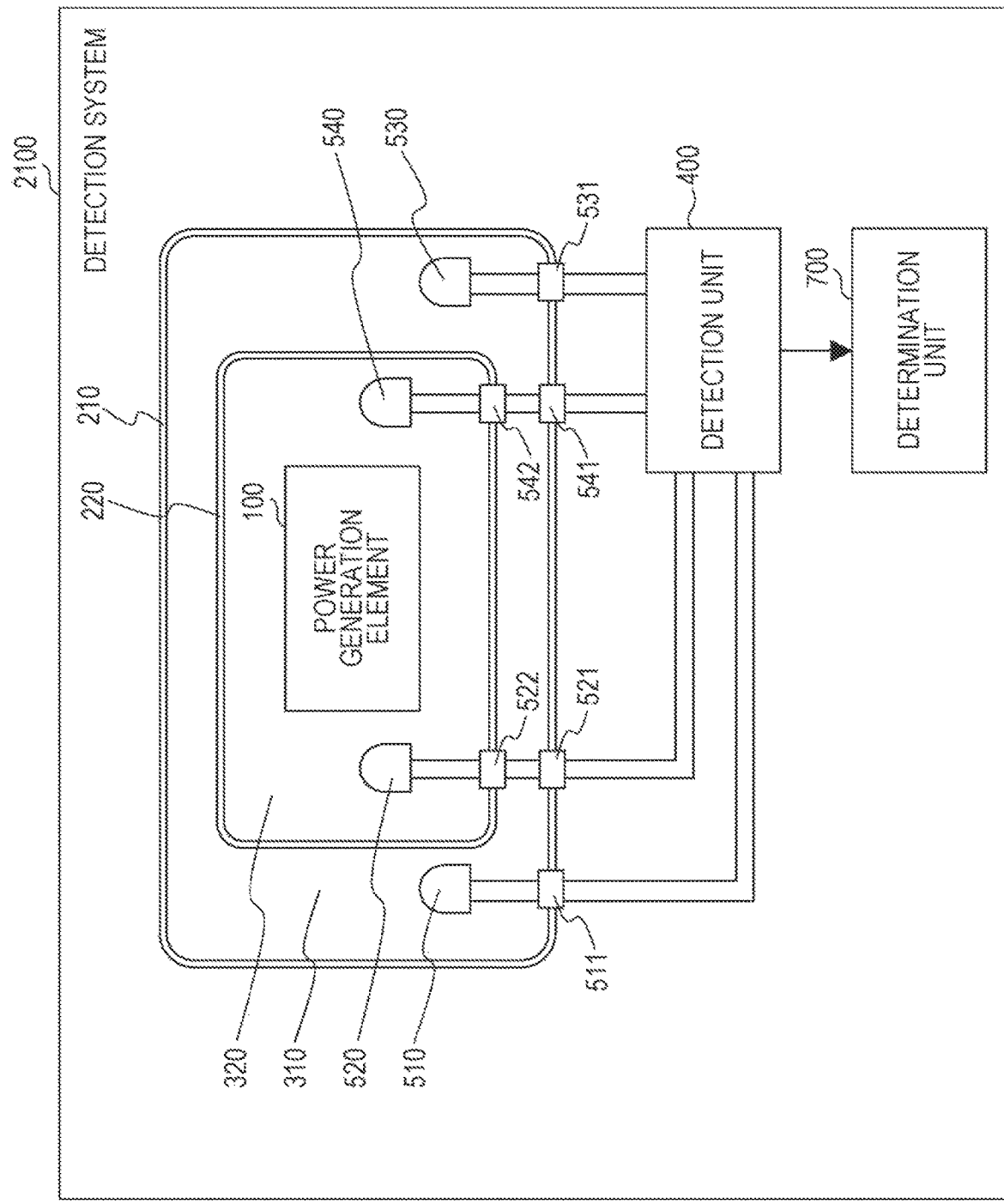
FIG. 13 illustrates a general configuration of a detection system according to the second embodiment.

FIG. 13 illustrates a general configuration of a detection system 2100 according to the second embodiment.

The detection system 2100 according to the second embodiment includes the following configuration in addition to the configuration of the detection system 1100 according to the above-described first embodiment and the determination unit 700.

That is, the detection system 2100 according to the second embodiment further include a third sensor element 530 and a fourth sensor element 540.

With the above-described configuration, sensor elements can detect respective target gases in a discriminated manner.

The third sensor element 530 is arranged in the first space section 310.

The detection unit 400 detects the generated gas in the first space section 310 on the basis of a detection signal from the third sensor element 530.

Also, as shown in FIG. 13, the third sensor element 530 may include a third connection line being a pair of connection lines connected with a sensing region of the third sensor element 530.

In the detection system 2100 according to the second embodiment, the third connection line passes through a sealing portion 531 provided at the first outer cover body 210 and extends to the outside of the first outer cover body 210.

The fourth sensor element 540 is arranged in the second space section 320.

The detection unit 400 detects the generated gas in the second space section 320 on the basis of a detection signal from the fourth sensor element 540.

Also, as shown in FIG. 13, the fourth sensor element 540 may include a fourth connection line being a pair of connection lines connected with a sensing region of the fourth sensor element 540.

In the detection system 2100 according to the second embodiment, the fourth connection line passes through a sealing portion 542 provided at the second outer cover body 220 and a sealing portion 541 provided at the first outer cover body 210, and extends to the outside of the first outer cover body 210.

The connection lines extending to the outside of the first outer cover body 210 are connected with the detection unit 400.

The detection unit 400 may individually output detection signals indicative of the detection results of the generated gas in the first space section 310 and the generated gas in the second space section 320 on the basis of the magnitudes of or changes in the voltages or currents detected respectively from the third and fourth connection lines.

It is to be noted that, if the generated gas is hydrogen sulfide gas, the third sensor element 530 and the fourth sensor element 540 may contain a resistance variable material the electrical resistance of which varies by chemical reaction to the hydrogen sulfide gas (for example, metal material such as copper).

It is to be noted that, in the second embodiment, the first sensor element 510 and the second sensor element 520 may detect the generated gas instead of providing the third sensor element 530 and the fourth sensor element 540. Alternatively, a gas analyzer may detect the generated gas like the detection system 1300 according to the above-described first embodiment.

An operation example of the detection system 2100 according to the second embodiment is described below.

If the hydrogen sulfide gas is generated from the power generation element 100 while the first outer cover body 210 or the second outer cover body 220 is not broken, the detection unit 400 detects an increase in concentration of the hydrogen sulfide gas in the second space section 320. In this state, the hydrogen sulfide gas does not immediately flow to the outside. However, for example, the use of the power generation element 100 may be stopped. Then, in a safety facility, the power generation element 100 may be recalled, discarded, or replaced, or may take another measurement.

If the hydrogen sulfide gas is generated from the power generation element 100 while only the second outer cover body 220 is broken, the detection unit 400 detects increases in concentration of the hydrogen sulfide gas and the second gas in the first space section 310, and increases in concentration of the hydrogen sulfide gas and the first gas in the second space section 320. In this state, the hydrogen sulfide gas flows to the outside immediately after the first outer cover body 210 is broken. Hence, for example, the use of the power generation element 100 may be stopped. Then, in a safety facility, the power generation element 100 may be recalled, discarded, or replaced, or may take another measurement.

If the hydrogen sulfide gas is generated from the power generation element 100 while only the first outer cover body 210 is broken, the detection unit 400 detects an increase in concentration of the hydrogen sulfide gas in the second space section 320, and an increase in concentration of the outside atmosphere in the first space section 310. In this state, the hydrogen sulfide gas flows to the outside immediately after the second outer cover body 220 is broken. Hence, for example, the use of the power generation element 100 may be stopped. Then, in a safety facility, the power generation element 100 may be recalled, discarded, or replaced, or may take another measurement.

If only the second outer cover body 220 is broken while the hydrogen sulfide gas is not generated from the power generation element 100, the detection unit 400 detects an increase in concentration of the second gas in the first space section 310, and an increase in concentration of the first gas in the second space section 320. In this state, the hydrogen sulfide gas does not immediately flow to the outside even if the hydrogen sulfide gas is generated from the power generation element 100. However, for example, the outer cover member may be replaced.

If only the first outer cover body 210 is broken while the hydrogen sulfide gas is not generated from the power generation element 100, the detection unit 400 detects an increase in concentration of the outside atmosphere in the first space section 310. In this state, the hydrogen sulfide gas does not immediately flow to the outside even if the hydrogen sulfide gas is generated from the power generation element 100. However, for example, the outer cover member may be replaced.

If the first outer cover body 210 and the second outer cover body 220 are broken while the hydrogen sulfide gas is not generated from the power generation element 100, the detection unit 400 detects increases in concentration of the second gas and the outside atmosphere in the first space section 310, and increases in concentration of the first gas and the outside atmosphere in the second space section 320. In this state, the hydrogen sulfide gas flows to the outside immediately after the hydrogen sulfide gas is generated from the power generation element 100. Hence, for example, the outer cover member may be replaced.

With the above-described configuration, the power generation element 100 can be operated with a high level of safety. At the time point at which the generated gas is detected, the risk of flow-out of the generated gas due to breakage or corrosion of the outer cover member is high. Hence, a quick and careful action is requested as a measure for safety of the power generation element 100. Also, if the first outer cover body 210 and the second outer cover body 220 are broken, generation of the generated gas immediately causes start of flow-out of the generated gas. Hence, the generated gas is detected easily at an early stage and the breakage of the outer cover member is addressed as described above. Accordingly, a system structure that detection of a generated gas does not directly result in serious danger can be provided. Also, a detection unit of a gas and an encapsulation structure of the gas can be simplified, and the cost used for the detection unit can be also decreased.

It is to be noted that, in the second embodiment, the determination unit 700 may be configured of, for example, an analog circuit or a digital circuit. The determination unit 700 may be configured of, for example, a processor and a memory. The processor may be, for example, a central processing unit (CPU) or a micro-processing unit (MPU). In this case, the processor may execute a control method (a determination method) disclosed in the present disclosure by reading out a program stored in the memory and executing the program.

For example, the memory (a storage device) of the determination unit 700 stores measurement data or command data. The stored data may be used for a condition of calculation by the processor of the determination unit 700. For example, if the memory stores time-lapse change data of gas concentration recorded therein, the gas concentration may be predicted to be a predetermined threshold or larger on the basis of the time-lapse change data. An abnormality can be determined by a method based on the transition state of a detection value.

Determination on an abnormal state by the determination unit 700 may be provided by a method based on a detection current value of a single detector, a method based on the transition state of a detection value by a single detector, a method based on calculation using detection values by a plurality of detectors, or a combination of these methods. For example, if the gas concentration detected by the detection unit 400 is a predetermined threshold or larger, the determination unit 700 can determine the abnormal state and type in accordance with these algorithms.

It is to be noted that, in the present disclosure, expression "a detection result of a detection unit 400 indicates a state in which a gas is detected" (detection of a gas is present) may include that "a detection result of a detection unit 400 indicates a state in which presence of a gas is detected," "a detection result of a detection unit 400 indicates a state in which a gas with a concentration being a predetermined threshold or larger is detected," and "a detection result of a detection unit 400 indicates a state in which an increase in concentration of a gas by an increase amount being a predetermined threshold or larger is detected."

Also, in the present disclosure, expression "a detection result of a detection unit 400 indicates a state in which gas is not detected" (detection of a gas is not present) may include that "a detection result of a detection unit 400 indicates a state in which presence of a gas is not detected," "a detection result of a detection unit 400 indicates a state in which a gas with a concentration being a predetermined threshold or larger is not detected," and "a detection result of a detection unit 400 indicates a state in which an increase in concentration of a gas by an increase amount being a predetermined threshold or larger is not detected."

Figure 14:
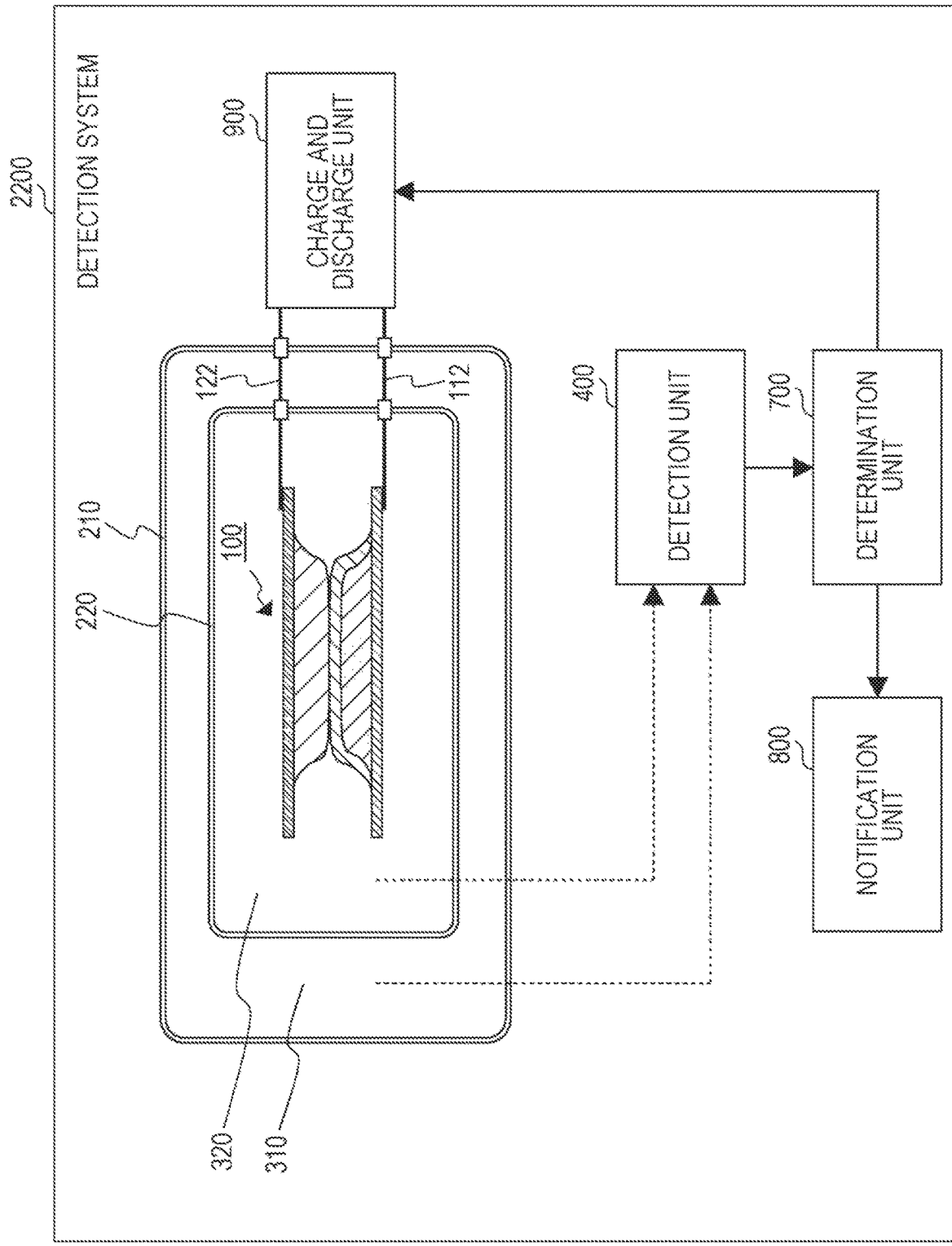
FIG. 14 illustrates a general configuration of a detection system according to the second embodiment.

FIG. 14 illustrates a general configuration of a detection system 2200 according to the second embodiment.

The detection system 2200 according to the second embodiment includes the following configuration in addition to the configuration of the detection system 2000 according to the above-described second embodiment.

That is, the detection system 2200 according to the second embodiment further includes a notification unit 800 and a charge and discharge unit 900.

The notification unit 800 receives an input of a determination result (a determination signal) of the determination unit 700. The notification unit 800 executes notification processing (transmission of a notification signal) on the basis of the determination result of the determination unit 700. For example, if the determination result of the determination unit 700 indicates a state in which at least one of the first outer cover body 210 and the second outer cover body 220 is broken, the notification unit 800 executes processing of making a notification about the breakage state.

The notification unit 800 may be, for example, a device that notifies a user or another object about the determination result of the determination unit 700 (for example, an indicator lamp, an indicator panel, or an alarm) or a device that transmits the determination result of the determination unit 700 to a remote terminal or server (for example, any type of various communication devices).

The charge and discharge unit 900 receives an input of the determination result (the determination signal) of the determination unit 700. The charge and discharge unit 900 is a device connected with the power generation element 100 through a lead wire or the like. The charge and discharge unit 900 controls charge and discharge with electric power on the basis of the determination result of the determination unit 700 (for example, stop of charge and discharge). For example, if the determination result of the determination unit 700 indicates a state in which at least one of the first outer cover body 210 and the second outer cover body 220 is broken, the charge and discharge unit 900 executes processing of stopping the charge and discharge.

The charge and discharge unit 900 may be, for example, a typically known charge and discharge device or an electric power conversion device that converts electric power (for example, an inverter or a converter).

With the above-described configuration, if the determination unit 700 detects an abnormality, for example, the notification unit 800 can be activated. Also, the determination unit 700 may transmit the stop signal to the charge and discharge unit 900 to stop the charge and discharge. Also, generation of an abnormality can be predicted at an early stage by monitoring or determining the operation state of the power generation element 100 on the basis of the transition state of the detection value. The prediction management is effective to prepare a measure to breakage of the outer cover member in a planned manner. Further, the prediction management can be used for providing previous notification about, for example, the timing of periodic maintenance. Accordingly, operation with a higher level of safety and a decrease in maintenance cost of a battery system using the power generation element 100 can be provided.

It is to be noted that, in the detection system 2200 according to the second embodiment, the determination unit 700 may determine the level of danger on the basis of the breakage states of the first outer cover body 210 and the second outer cover body 220.

That is, the determination unit 700 may determine that the state in which both the first outer cover body 210 and the second outer cover body 220 are broken (case D) is a state with the highest level of danger (first danger level).

Further, the determination unit 700 may determine that the state in which the first outer cover body 210 is not broken and the second outer cover body 220 is broken (case C) is a state with a high level of danger next to the first danger level (second danger level). This is because hydrogen sulfide may be generated with higher possibility in the case C than that in the case B.

Further, the determination unit 700 may determine that the state in which the first outer cover body 210 is broken and the second outer cover body 220 is not broken (case B) is a state with a high level of danger next to the second danger level (third danger level).

Further, the determination unit 700 may determine that the state in which neither the first outer cover body 210 nor the second outer cover body 220 is broken (case A) is a state with the lowest level of danger (fourth danger level).

Also, in the detection system 2200 according to the second embodiment, the notification unit 800 may be controlled in accordance with the above-described danger level. That is, for example, the notification unit 800 may change, for example, the notification method and notification frequency, in accordance with the above-described danger level.

Also, in the detection system 2200 according to the second embodiment, the charge and discharge unit 900 may be controlled in accordance with the above-described danger level. That is, for example, the charge and discharge unit 900 may change, for example, the stop method and stop time of charge and discharge, in accordance with the above-described danger level.

As described above, since the first outer cover body 210 and the second outer cover body 220 provide the double outer cover structure, and the breakage states of the first outer cover body 210 and the second outer cover body 220 can be individually determined, the danger level can be determined stepwise. Accordingly, operation with a higher level of safety and a decrease in maintenance cost of the battery system using the power generation element 100 can be provided.

Third Embodiment

A third embodiment is described below. The redundant description provided in the above-described first or second embodiment is properly omitted.

Figure 15:
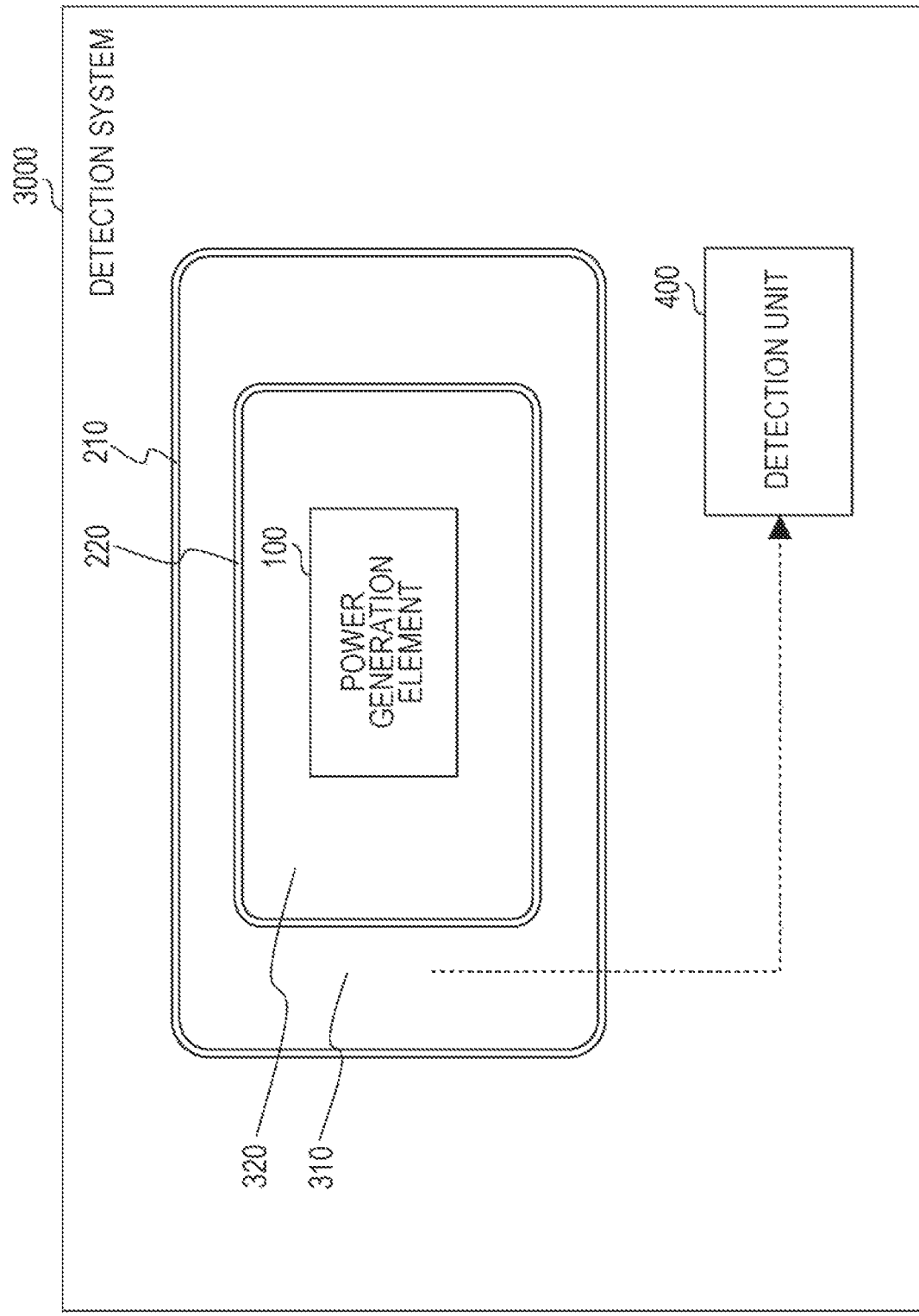
FIG. 15 illustrates a general configuration of a detection system according to a third embodiment.

FIG. 15 illustrates a general configuration of a detection system 3000 according to the third embodiment.

The detection system 3000 according to the third embodiment includes a power generation element 100, a first outer cover body 210, a second outer cover body 220, a first space section 310, a second space section 320, and a detection unit 400.

The first outer cover body 210 envelops the power generation element 100 and the second outer cover body 220.

The second outer cover body 220 is located between the power generation element 100 and the first outer cover body 210. The second outer cover body 220 envelops the power generation element 100.

The first space section 310 is a space enclosed (for example, hermetically sealed) by the first outer cover body 210 and the second outer cover body 220.

The second space section 320 is a space enclosed (for example, hermetically sealed) by the second outer cover body 220.

The detection unit 400 detects "a gas in the first space section 310."

A second gas is encapsulated in the second space section 320.

The detection unit 400 detects an outside atmosphere entering from the outside of the first outer cover body 210 and the second gas, in the first space section 310.

With the above-described configuration, the detection accuracy of the breakage state of the outer cover member enveloping the power generation element 100 can be increased. To be specific, the presence of breakage of the first outer cover body 210 and the second outer cover body 220 can be detected on the basis of the detection result of the outside atmosphere and the detection result of the second gas in the first space section 310. Accordingly, the generation of breakage of the first outer cover body 210 and the second outer cover body 220 can be detected with high accuracy at an early stage. Hence, for example, if at least one of the first outer cover body 210 and the second outer cover body 220 is broken, a measure of stopping use of the power generation element 100 or another measure can be executed at an early stage. Accordingly, the safety of the system using the power generation element 100 can be increased.

Also, with the above-described configuration, the first outer cover body 210 and the second outer cover body 220 can provide a double outer cover structure. Accordingly, resistance to an impact from the outside of the outer cover bodies, and impermeability to water can be increased. Further, a generated gas (for example, hydrogen sulfide gas) generated from the power generation element 100 over long-term use of the power generation element 100 can be prevented from leaking to the outside.

Also, with the above-described configuration, a detection target space section for detecting the breakage state of the outer cover member can be set at only the first space section 310. Hence, for example, the sensor element for detecting the gas in the second space section 320 may be omitted. Hence, the configuration of the detection unit 400 can be further simplified as compared with the configuration using both the first space section 310 and the second space section 320 as the detection target space sections.

Figure 16:
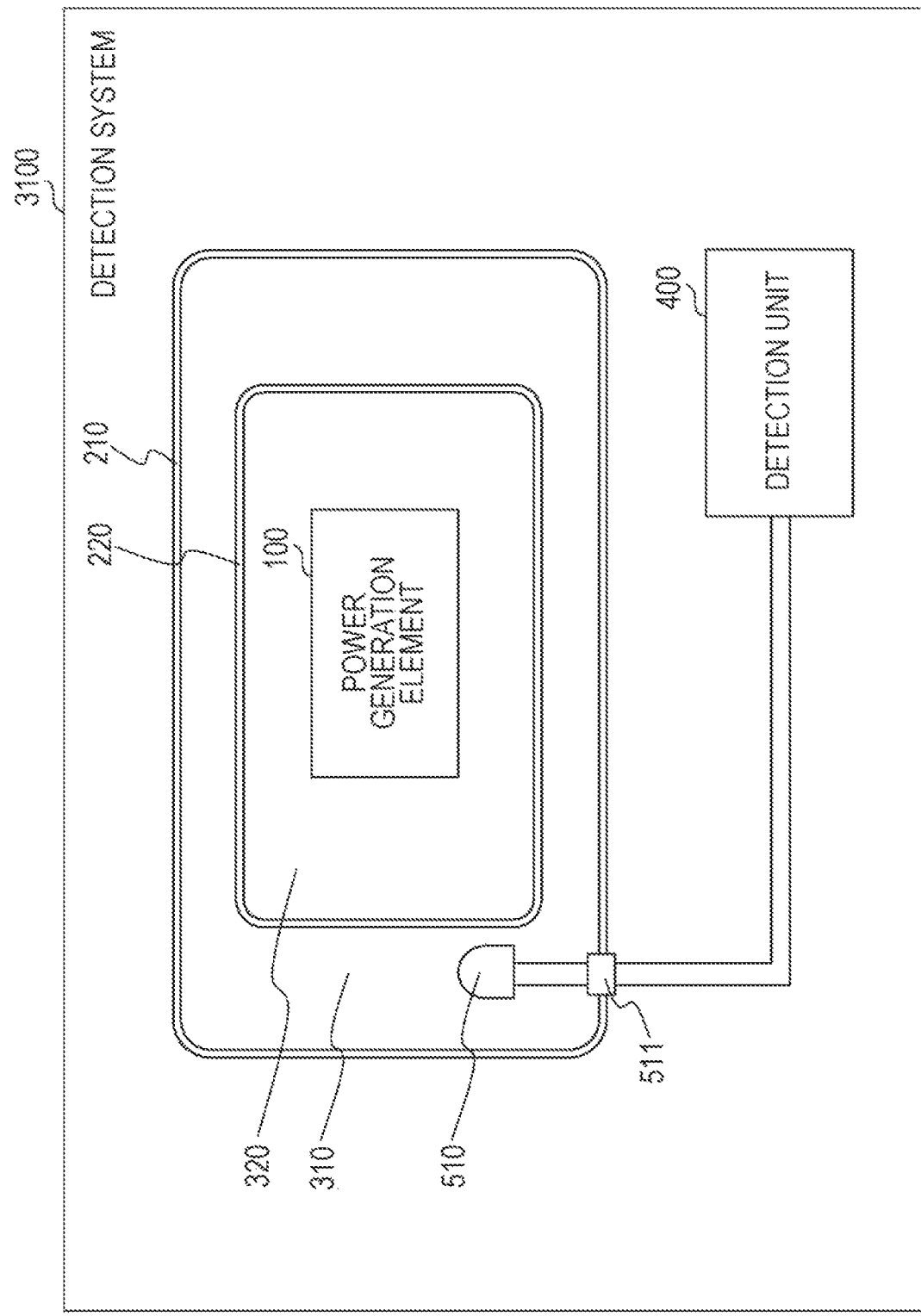
FIG. 16 illustrates a general configuration of a detection system according to the third embodiment.

FIG. 16 illustrates a general configuration of a detection system 3100 according to the third embodiment.

The detection system 3100 according to the third embodiment further includes a first sensor element 510 in addition to the configuration of the above-described detection system 3000.

The first sensor element 510 is arranged in the first space section 310.

The detection unit 400 detects the outside atmosphere and the second gas in the first space section 310 on the basis of a detection signal from the first sensor element 510.

With the above-described configuration, the detection system can be decreased in size as compared with a configuration (a detection system 3200, described later) including a communicating tube that causes the inside of the outer cover member to communicate with the detection unit 400.

Figure 17:
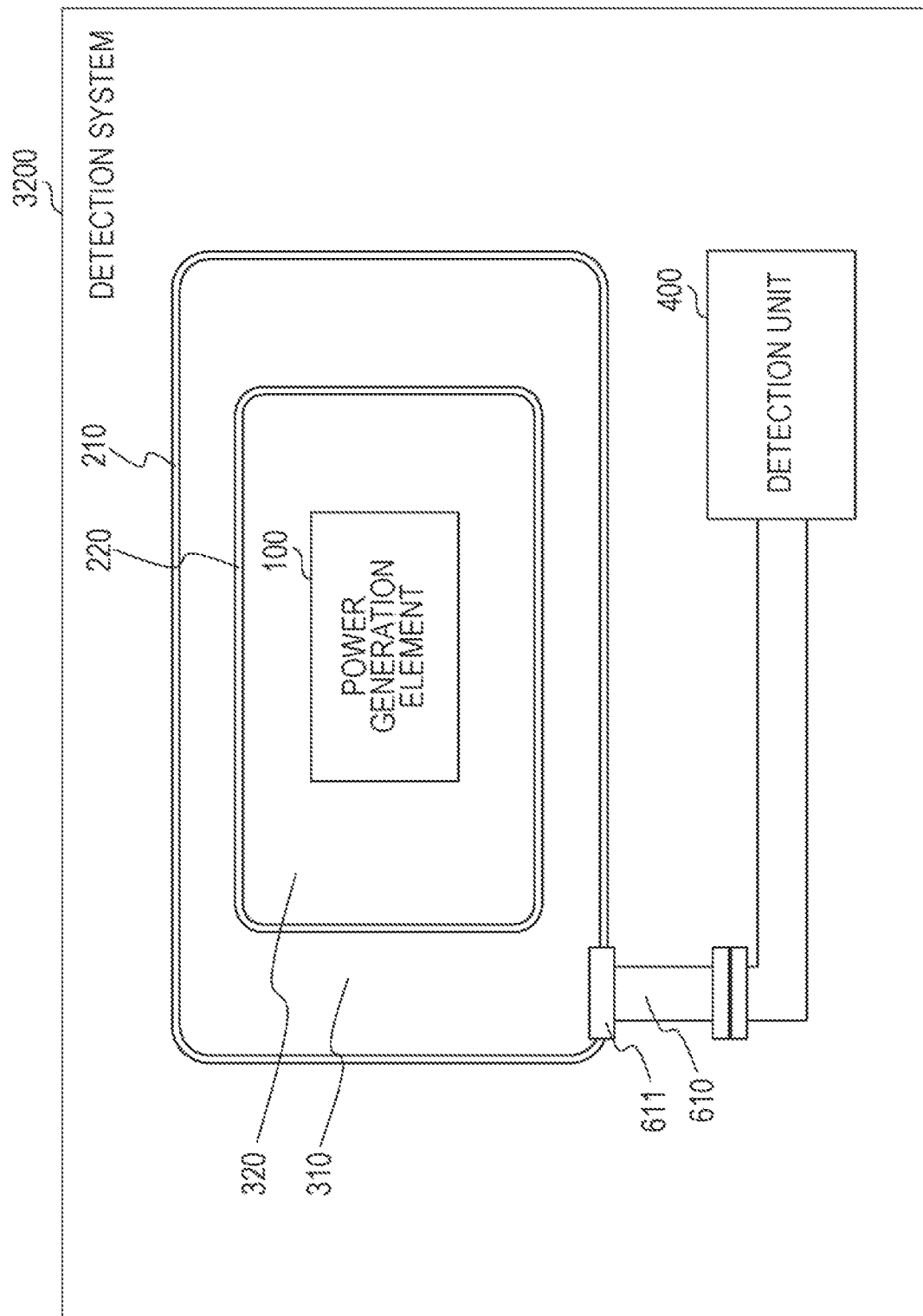
FIG. 17 illustrates a general configuration of a detection system according to the third embodiment.

FIG. 17 illustrates a general configuration of a detection system 3200 according to the third embodiment.

The detection system 3200 according to the third embodiment further includes a first communicating tube 610 in addition to the configuration of the above-described detection system 3000.

The first communicating tube 610 causes the first space section 310 to communicate with the detection unit 400.

The detection unit 400 detects the outside atmosphere and the second gas in the first space section 310 introduced through the first communicating tube 610.

With the above-described configuration, a detection device or the like with higher detection sensitivity may be provided as the detection unit 400 outside the outer cover member as compared with the configuration provided with the sensor element in the outer cover member (the above-described detection system 3100). Accordingly, the detection accuracy of the breakage state of the outer cover member enveloping the power generation element 100 can be further increased.

Respective components according to the third embodiment may properly use the respective components according to the above-described first embodiment.

Fourth Embodiment

A fourth embodiment is described below. The redundant description provided in any one of the above-described first to third embodiments is properly omitted.

Figure 18:
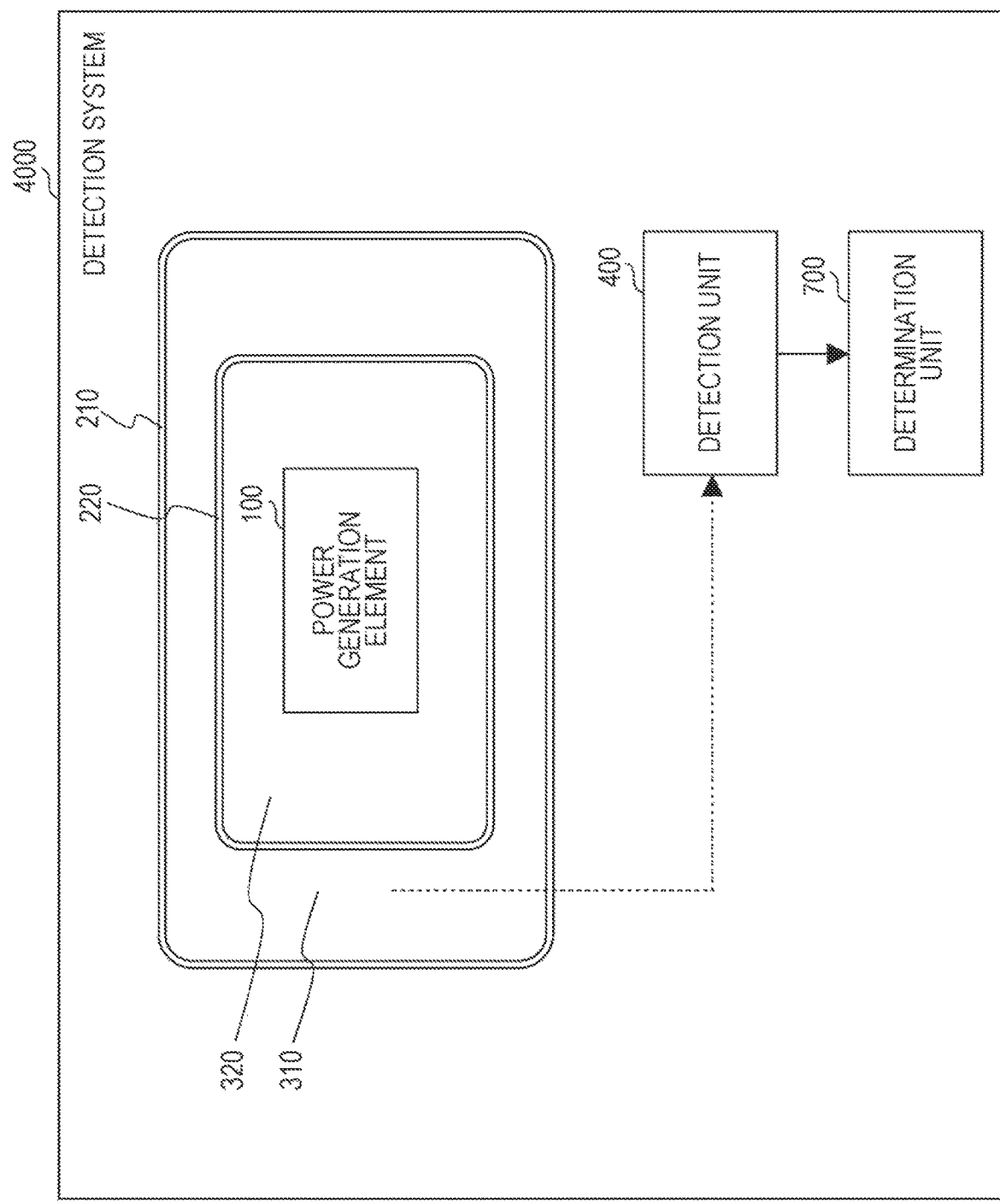
FIG. 18 illustrates a general configuration of a detection system according to a fourth embodiment.

FIG. 18 illustrates a general configuration of a detection system 4000 according to the fourth embodiment.

The detection system 4000 according to the fourth embodiment includes the following configuration in addition to the configuration of the detection system according to the above-described third embodiment.

That is, the detection system 4000 according to the fourth embodiment further includes a determination unit 700.

The determination unit 700 determines the breakage states of the first outer cover body 210 and the second outer cover body 220 on the basis of the detection result of the detection unit 400.

FIG. 19 illustrates a determination method of a determination unit 700 according to the fourth embodiment.

In the detection system 4000 according to the fourth embodiment, the determination unit 700 may execute the determination method shown in FIG. 19.

That is, if the detection result of the detection unit 400 indicates a state in which the outside atmosphere is not detected in the first space section 310 and the second gas is not detected in the first space section 310, the determination unit 700 determines that neither the first outer cover body 210 nor the second outer cover body 220 is broken (case A-40).

Also, if the detection result of the detection unit 400 indicates a state in which the outside atmosphere is detected in the first space section 310 and the second gas is not detected in the first space section 310, the determination unit 700 determines that the first outer cover body 210 is broken and the second outer cover body 220 is not broken (case B-40).

Also, if the detection result of the detection unit 400 indicates a state in which the outside atmosphere is not detected in the first space section 310 and the second gas is detected in the first space section 310, the determination unit 700 determines that the first outer cover body 210 is not broken and the second outer cover body 220 is broken (case C-40).

Also, if the detection result of the detection unit 400 indicates a state in which the outside atmosphere is detected in the first space section 310 and the second gas is detected in the first space section 310, the determination unit 700 determines that both the first outer cover body 210 and the second outer cover body 220 are broken (case D-40).

With the above-described configuration, the determination accuracy of the breakage state of the outer cover member enveloping the power generation element 100 can be increased. To be specific, the presence of breakage of the first outer cover body 210 and the second outer cover body 220 can be individually determined on the basis of the detection result of the outside atmosphere and the detection result of the second gas in the first space section 310. Accordingly, the generation of breakage of the first outer cover body 210 and the second outer cover body 220 can be determined with high accuracy at an early stage.

It is to be noted that, in the detection system 4000 according to the fourth embodiment, the power generation element 100 may contain a material which contributes to generation of a generated gas.

The detection unit 400 may detect the generated gas in the first space section 310.

With the above-described configuration, the detection accuracy of the breakage state of the outer cover member enveloping the power generation element 100 can be increased. To be specific, the presence of breakage of the second outer cover body 220 can be detected on the basis of the detection result of the generated gas which may be generated in the second space section 320. Accordingly, the generation of breakage of the second outer cover body 220 can be detected with higher accuracy at an earlier stage. Hence, for example, if the second outer cover body 220 is broken, a measure of stopping use of the power generation element 100 or another measure can be executed at an early stage. Accordingly, in particular, even if the generated gas is a toxic gas (for example, hydrogen sulfide gas), the safety of the system using the power generation element 100 can be maintained.

It is to be noted that, in the detection system 4000 according to the fourth embodiment, the determination unit 700 may further execute the following determination method.

That is, if the detection result of the detection unit 400 indicates a state in which the generated gas is not detected in the first space section 310, the determination unit 700 determines that the second outer cover body 220 is not broken.

Also, if the detection result of the detection unit 400 indicates a state in which the generated gas is detected in the first space section 310, the determination unit 700 determines that the second outer cover body 220 is broken.

With the above-described configuration, the determination accuracy of the breakage state of the outer cover member enveloping the power generation element 100 can be further increased. To be specific, the presence of breakage of the second outer cover body 220 can be determined on the basis of the detection result of the generated gas in the first space section 310. Accordingly, the generation of breakage of the second outer cover body 220 can be determined with higher accuracy at an earlier stage.

It is to be noted that the determination method based on the detection result of the generated gas may be executed in combination with the determination method illustrated in aforementioned FIG. 19.

In this case, if the determination result of the determination method based on the detection result of the generated gas differs from the determination result of the determination method illustrated in aforementioned FIG. 19, the determination result of the determination method based on the detection result of the generated gas may have priority (may be employed). Accordingly, even if the generated gas continuously issues to the outside of the outer cover member and hence the outside atmosphere cannot flow to the inside of the outer cover member, since the determination is based on the detection result of the generated gas, the determination accuracy of the breakage state of the outer cover member can be further increased.

Alternatively, if the determination result of the determination method based on the detection result of the generated gas differs from the determination result of the determination method illustrated in aforementioned FIG. 19, the determination result of the determination method illustrated in aforementioned FIG. 19 may have priority (may be employed). Accordingly, even if the generation amount of the generated gas is very small and hence the generated gas cannot sufficiently flow into the first space section 310, since the determination is based on the detection result of a gas other than the generated gas, the determination accuracy of the breakage state of the outer cover member can be further increased.

Figure 20:
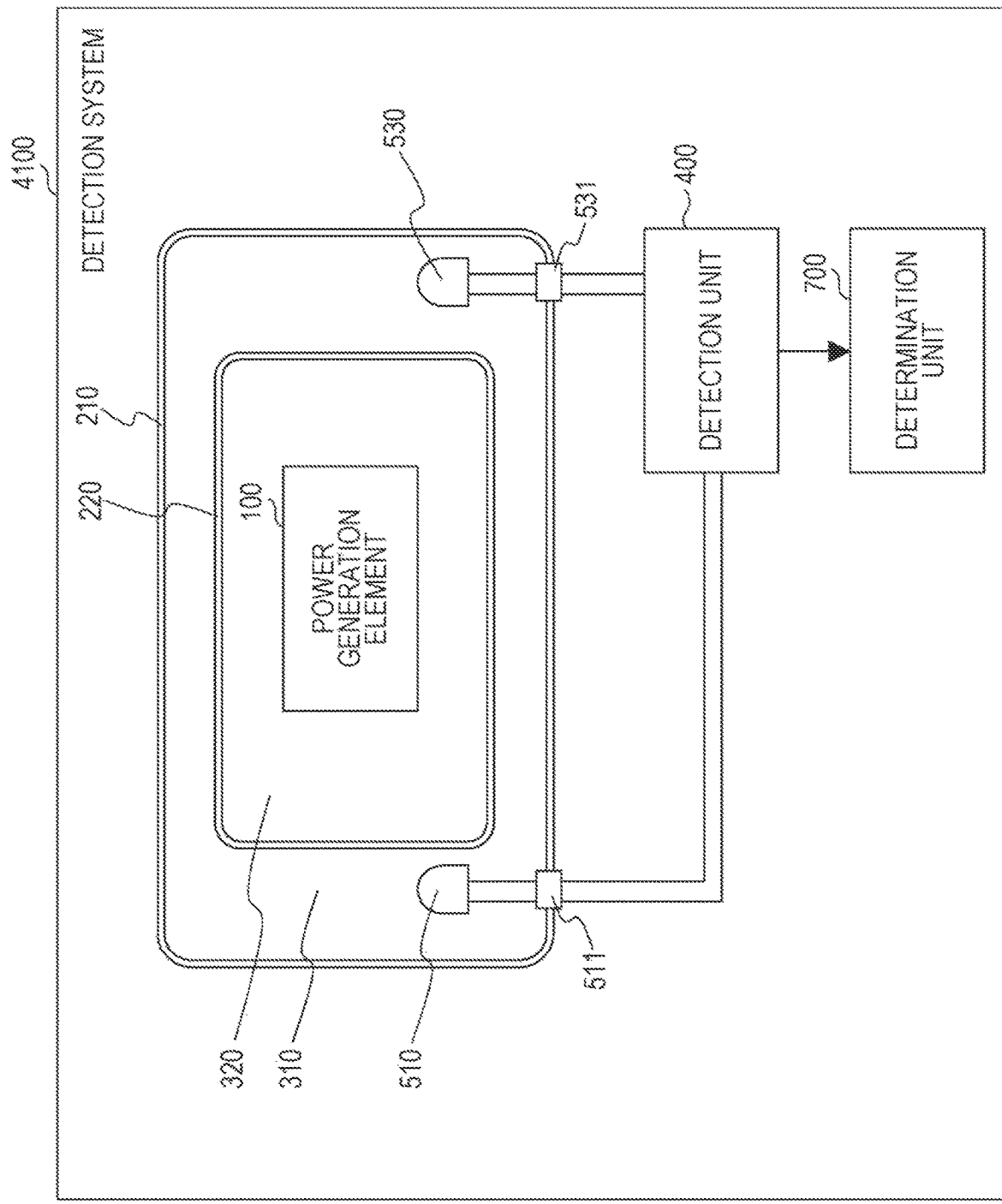
FIG. 20 illustrates a general configuration of a detection system according to the fourth embodiment.

FIG. 20 illustrates a general configuration of a detection system 4100 according to the fourth embodiment.

The detection system 4100 according to the fourth embodiment includes the following configuration in addition to the configuration of the detection system 3100 according to the above-described third embodiment and the determination unit 700.

That is, the detection system 4100 according to the fourth embodiment further includes a third sensor element 530.

With the above-described configuration, a sensor element can detect a target gas in a discriminated manner.

The third sensor element 530 is arranged in the first space section 310.

The detection unit 400 detects a generated gas in the first space section 310 on the basis of a detection signal from the third sensor element 530.

Also, as shown in FIG. 20, the third sensor element 530 may include a third connection line being a pair of connection lines connected with a sensing region of the third sensor element 530.

In the detection system 4100 according to the fourth embodiment, the third connection line passes through a sealing portion 531 provided at the first outer cover body 210 and extends to the outside of the first outer cover body 210.

The third connection line extending to the outside of the first outer cover body 210 is connected with the detection unit 400.

The detection unit 400 may output a detection signal indicative of the detection result of the generated gas in the first space section 310 on the basis of the magnitude of or change in the voltage or current detected from the third connection line.

It is to be noted that, if the generated gas is hydrogen sulfide gas, the third sensor element 530 may contain a resistance variable material the electrical resistance of which varies by chemical reaction to the hydrogen sulfide gas (for example, metal material such as copper).

It is to be noted that, in the fourth embodiment, the first sensor element 510 may detect the generated gas instead of providing the third sensor element 530. Alternatively, a gas analyzer may detect the generated gas like the detection system 3200 according to the above-described third embodiment.

Respective components according to the fourth embodiment may properly use the respective components according to the above-described second embodiment.

Fifth Embodiment

A fifth embodiment is described below. The redundant description provided in any one of the above-described first to fourth embodiments is properly omitted.

Figure 21:
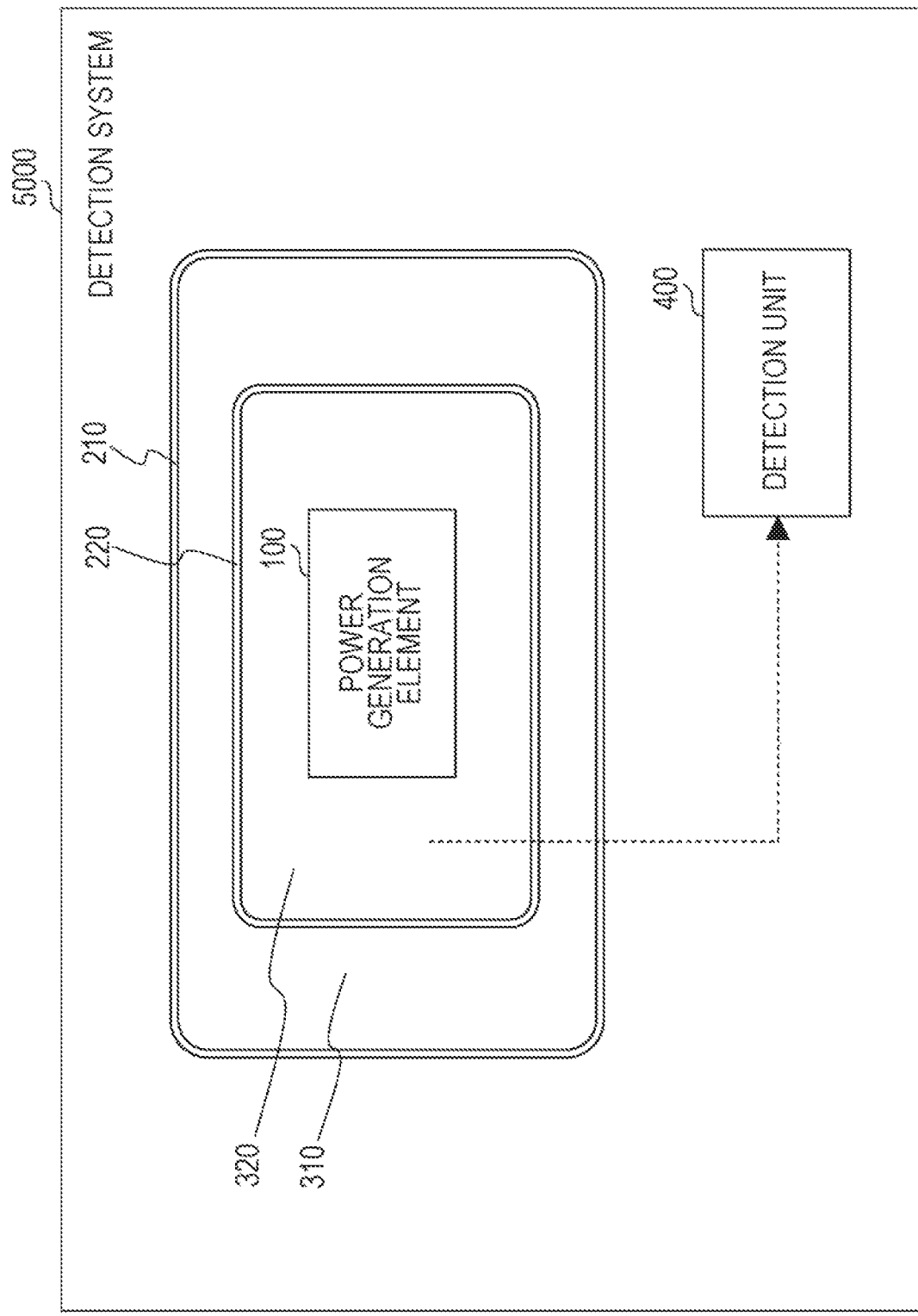
FIG. 21 illustrates a general configuration of a detection system according to a fifth embodiment.

FIG. 21 illustrates a general configuration of a detection system 5000 according to the fifth embodiment.

The detection system 5000 according to the fifth embodiment includes a power generation element 100, a first outer cover body 210, a second outer cover body 220, a first space section 310, a second space section 320, and a detection unit 400.

The first outer cover body 210 envelops the power generation element 100 and the second outer cover body 220.

The second outer cover body 220 is located between the power generation element 100 and the first outer cover body 210. The second outer cover body 220 envelops the power generation element 100.

The first space section 310 is a space enclosed (for example, hermetically sealed) by the first outer cover body 210 and the second outer cover body 220.

The second space section 320 is a space enclosed (for example, hermetically sealed) by the second outer cover body 220.

The detection unit 400 detects "a gas in the second space section 320."

A first gas is encapsulated in the first space section 310.

The detection unit 400 detects an outside atmosphere entering from the outside of the first outer cover body 210 and the first gas in the second space section 320.

With the above-described configuration, the detection accuracy of the breakage state of the outer cover member enveloping the power generation element 100 can be increased. To be specific, the presence of breakage of the first outer cover body 210 and the second outer cover body 220 can be detected on the basis of the detection result of the outside atmosphere and the detection result of the first gas in the second space section 320. Accordingly, the generation of breakage of the first outer cover body 210 and the second outer cover body 220 can be detected with high accuracy at an early stage. Hence, for example, if only the second outer cover body 220 is broken or if both the first outer cover body 210 and the second outer cover body 220 are broken, a measure of stopping use of the power generation element 100 or another measure can be executed at an early stage. Accordingly, the safety of the system using the power generation element 100 can be increased.

Also, with the above-described configuration, the first outer cover body 210 and the second outer cover body 220 can provide a double outer cover structure. Accordingly, resistance to an impact from the outside of the outer cover bodies, and impermeability to water can be increased. Further, a generated gas (for example, hydrogen sulfide gas) generated from the power generation element 100 over long-term use of the power generation element 100 can be prevented from leaking to the outside.

Also, with the above-described configuration, a detection target space section for detecting the breakage state of the outer cover member can be set at only the second space section 320. Hence, for example, the sensor element for detecting the gas in the first space section 310 may be omitted. Hence, the configuration of the detection unit 400 can be further simplified as compared with the configuration using both the first space section 310 and the second space section 320 as the detection target space sections.

Figure 22:
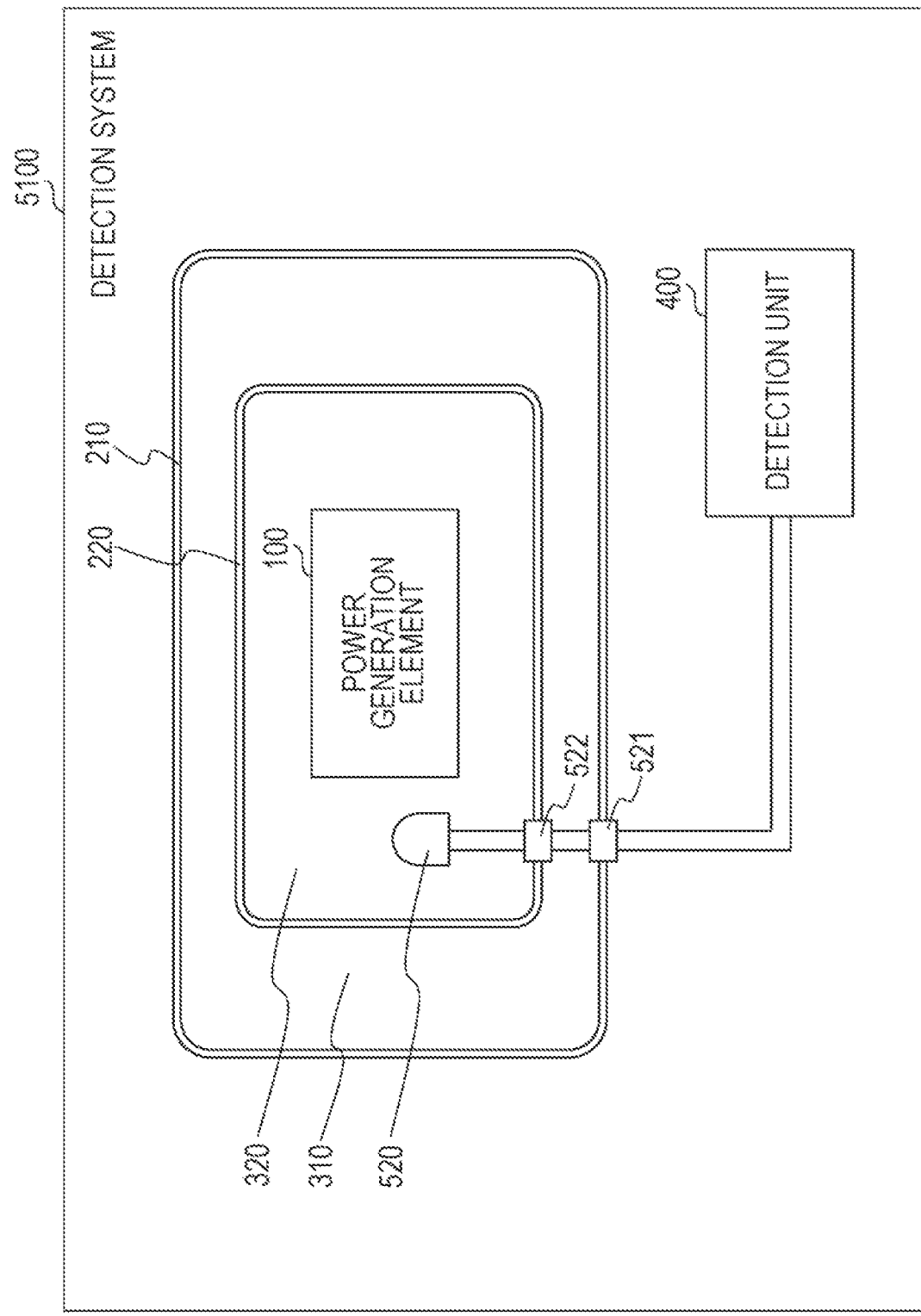
FIG. 22 illustrates a general configuration of a detection system according to the fifth embodiment.

FIG. 22 illustrates a general configuration of a detection system 5100 according to the fifth embodiment.

The detection system 5100 according to the fifth embodiment further includes a second sensor element 520 in addition to the configuration of the above-described detection system 5000.

The second sensor element 520 is arranged in the second space section 320.

The detection unit 400 detects an outside atmosphere and a first gas in the second space section 320 on the basis of a detection signal from the second sensor element 520.

With the above-described configuration, the detection system can be decreased in size as compared with a configuration (a detection system 5300, described later) including a communicating tube that causes the inside of the outer cover member to communicate with the detection unit 400.

Figure 23:
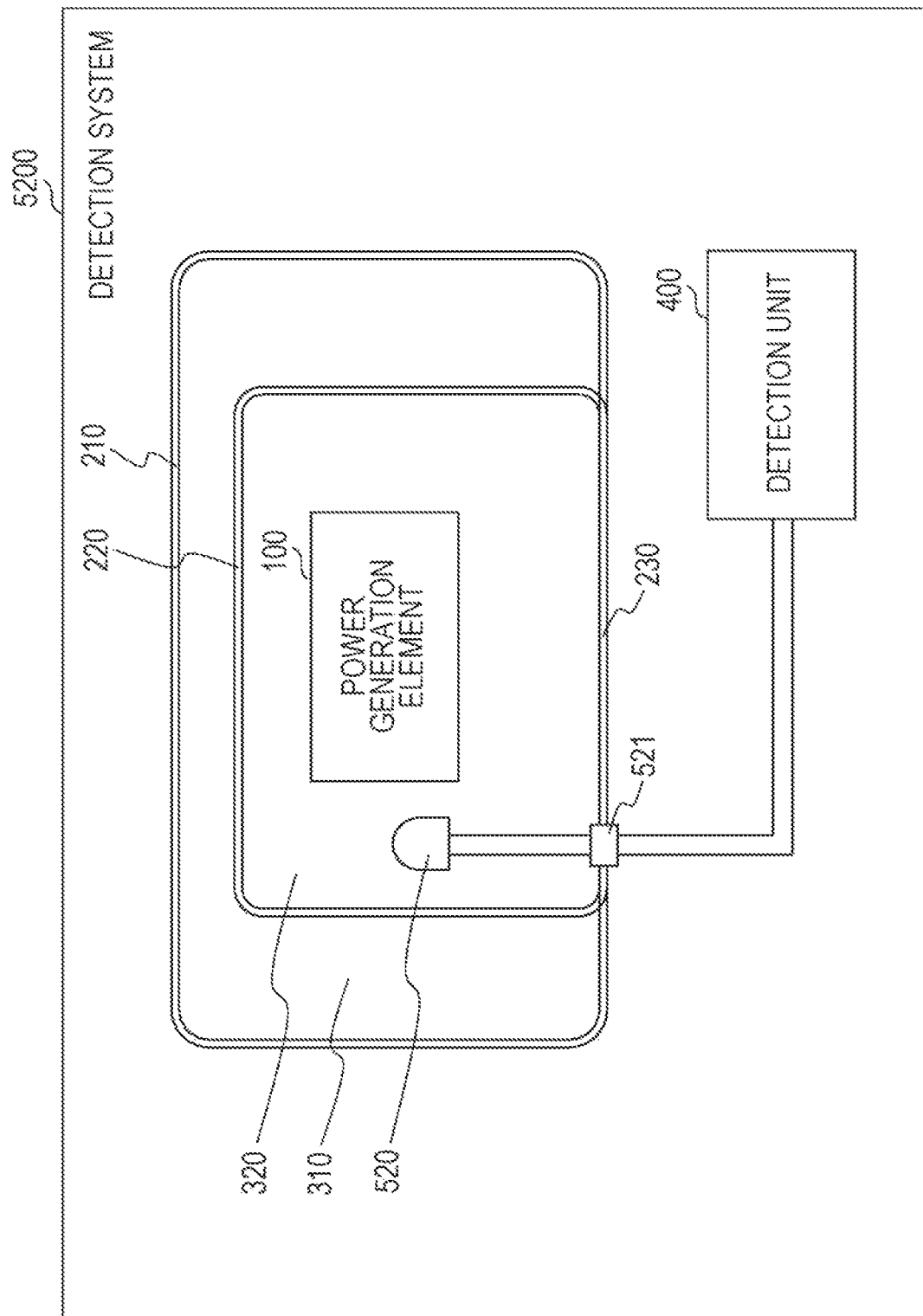
FIG. 23 illustrates a general configuration of a detection system according to the fifth embodiment.

FIG. 23 illustrates a general configuration of a detection system 5200 according to the fifth embodiment.

The detection system 5200 according to the fifth embodiment includes the following configuration in addition to the configuration of the above-described detection system 5100.

That is, in the detection system 5200 according to the fifth embodiment, a portion of the first outer cover body 210 and a portion of the second outer cover body 220 are integrated with one another and form a common outer cover portion 230.

The second connection line connected with the second sensor element 520 extends through the common outer cover portion 230 and is connected with the detection unit 400. In other words, the sealing portion 521 from which the second connection line extends is provided at the common outer cover portion 230.

With the above-described configuration, the number of sealing portions to cause the second connection line of the second sensor element 520 to extend to the outside of the outer cover member can be decreased. Accordingly, the processing step for the sealing portion can be simplified, and the processing cost of the sealing portion can be decreased. Also, a decrease in strength due to presence of a plurality of sealing portions can be prevented from occurring. Accordingly, the risk of breakage of the outer cover member can be decreased.

Figure 24:
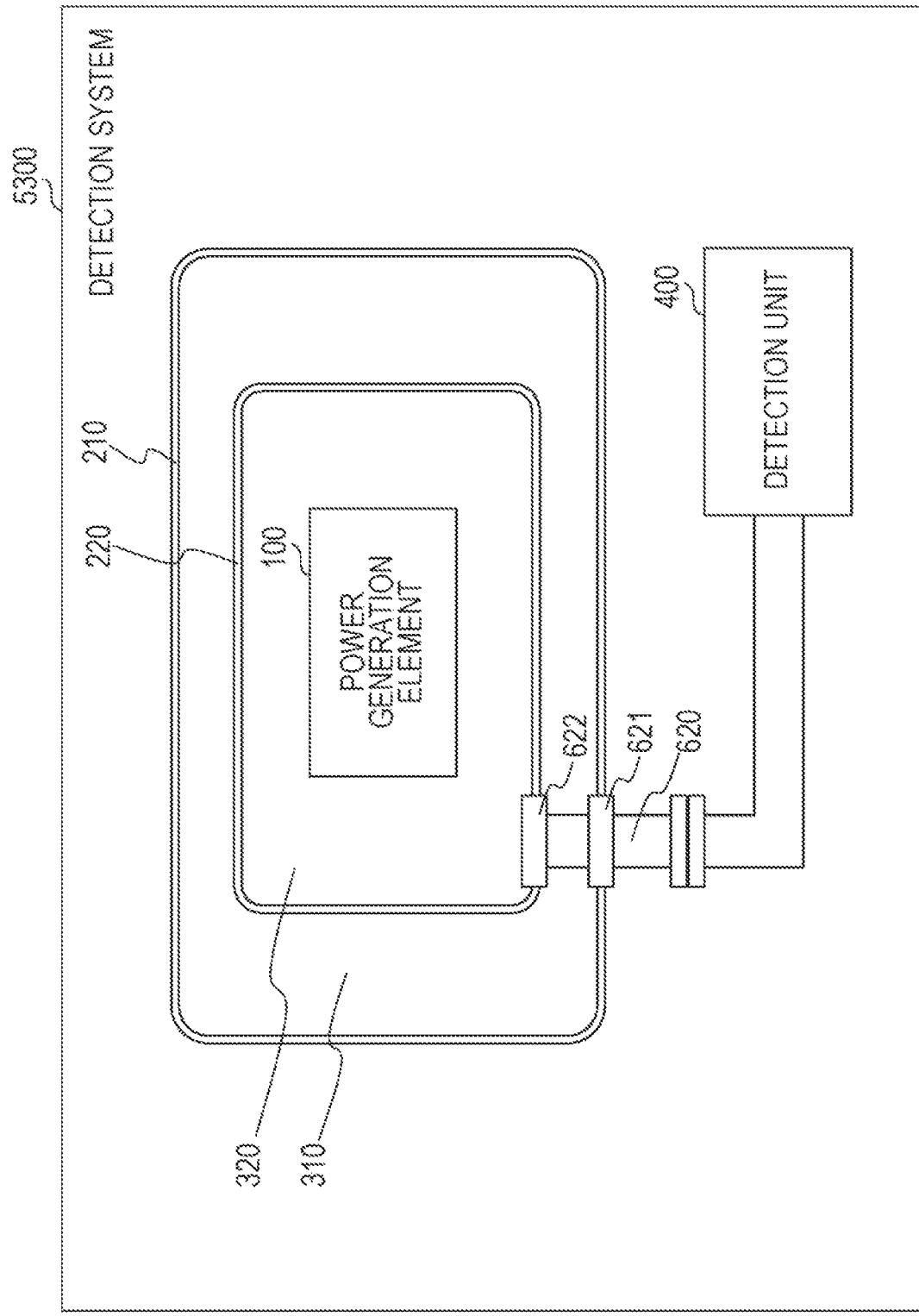
FIG. 24 illustrates a general configuration of a detection system according to the fifth embodiment.

FIG. 24 illustrates a general configuration of a detection system 5300 according to the fifth embodiment.

The detection system 5300 according to the fifth embodiment further includes a second communicating tube 620 in addition to the configuration of the above-described detection system 5000.

The second communicating tube 620 causes the second space section 320 to communicate with the detection unit 400.

The detection unit 400 detects an outside atmosphere and a first gas in the second space section 320 introduced through the second communicating tube 620.

With the above-described configuration, a detection device or the like with higher detection sensitivity may be provided as the detection unit 400 outside the outer cover member as compared with the configuration provided with the sensor element in the outer cover member (the above-described detection system 5100). Accordingly, the detection accuracy of the breakage state of the outer cover member enveloping the power generation element 100 can be further increased.

Figure 25:
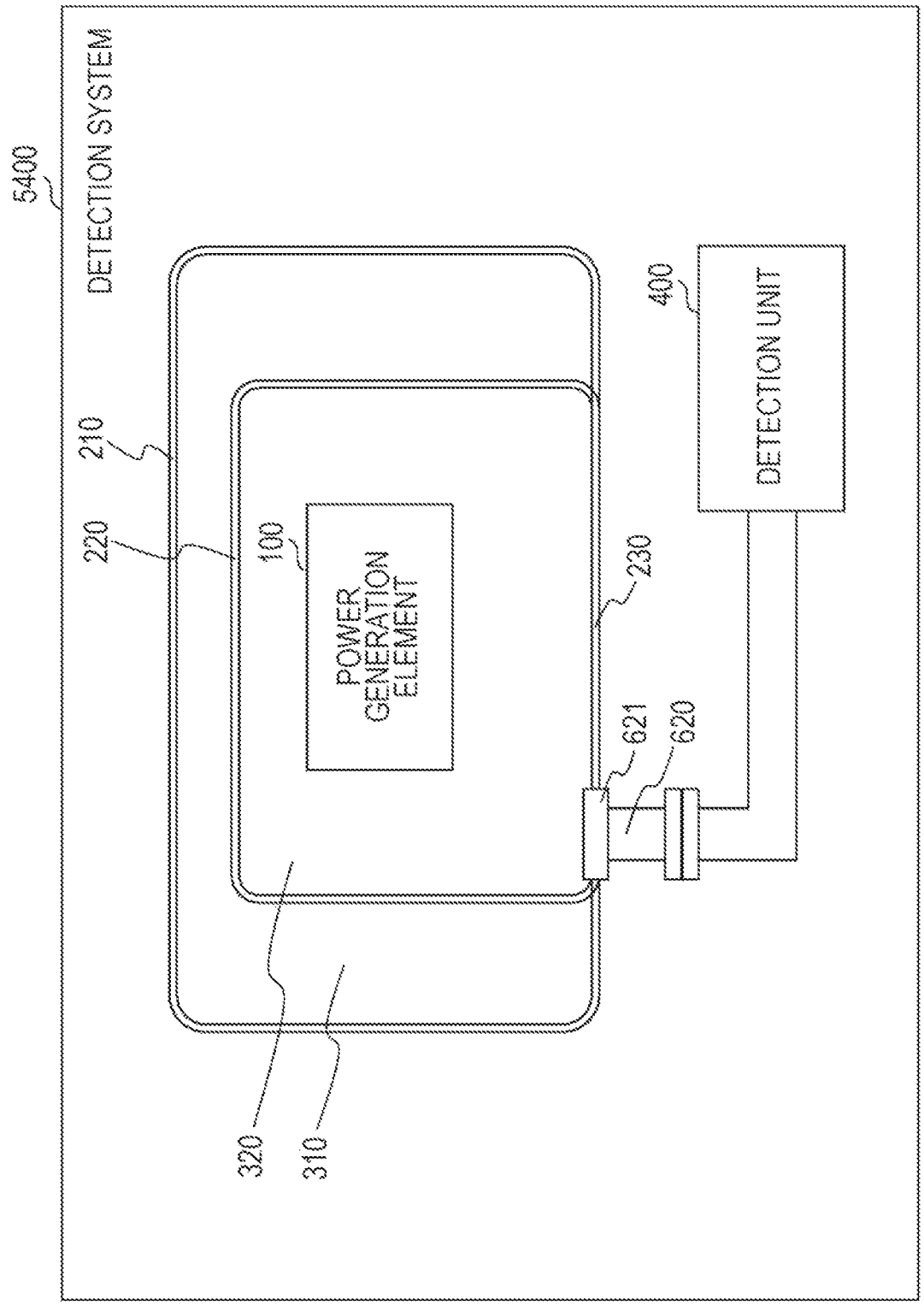
FIG. 25 illustrates a general configuration of a detection system according to the fifth embodiment.

FIG. 25 illustrates a general configuration of a detection system 5400 according to the fifth embodiment.

The detection system 5400 according to the fifth embodiment includes the following configuration in addition to the configuration of the above-described detection system 5300.

That is, in the detection system 5400 according to the fifth embodiment, a portion of the first outer cover body 210 and a portion of the second outer cover body 220 are integrated with one another and form a common outer cover portion 230.

A second communicating tube 620 is coupled with the common outer cover portion 230.

With the above-described configuration, the number of coupling portions between the second communicating tube 620 and the outer cover member can be decreased. Accordingly, the arrangement step for the coupling portion can be simplified, and the arrangement cost of the coupling portion can be decreased. Also, a decrease in strength due to presence of a plurality of coupling portions can be prevented from occurring. Accordingly, the risk of breakage of the outer cover member can be decreased.

Respective components according to the fifth embodiment may properly use the respective components according to the above-described first embodiment.

Sixth Embodiment

A sixth embodiment is described below. The redundant description provided in any one of the above-described first to fifth embodiments is properly omitted.

Figure 26:
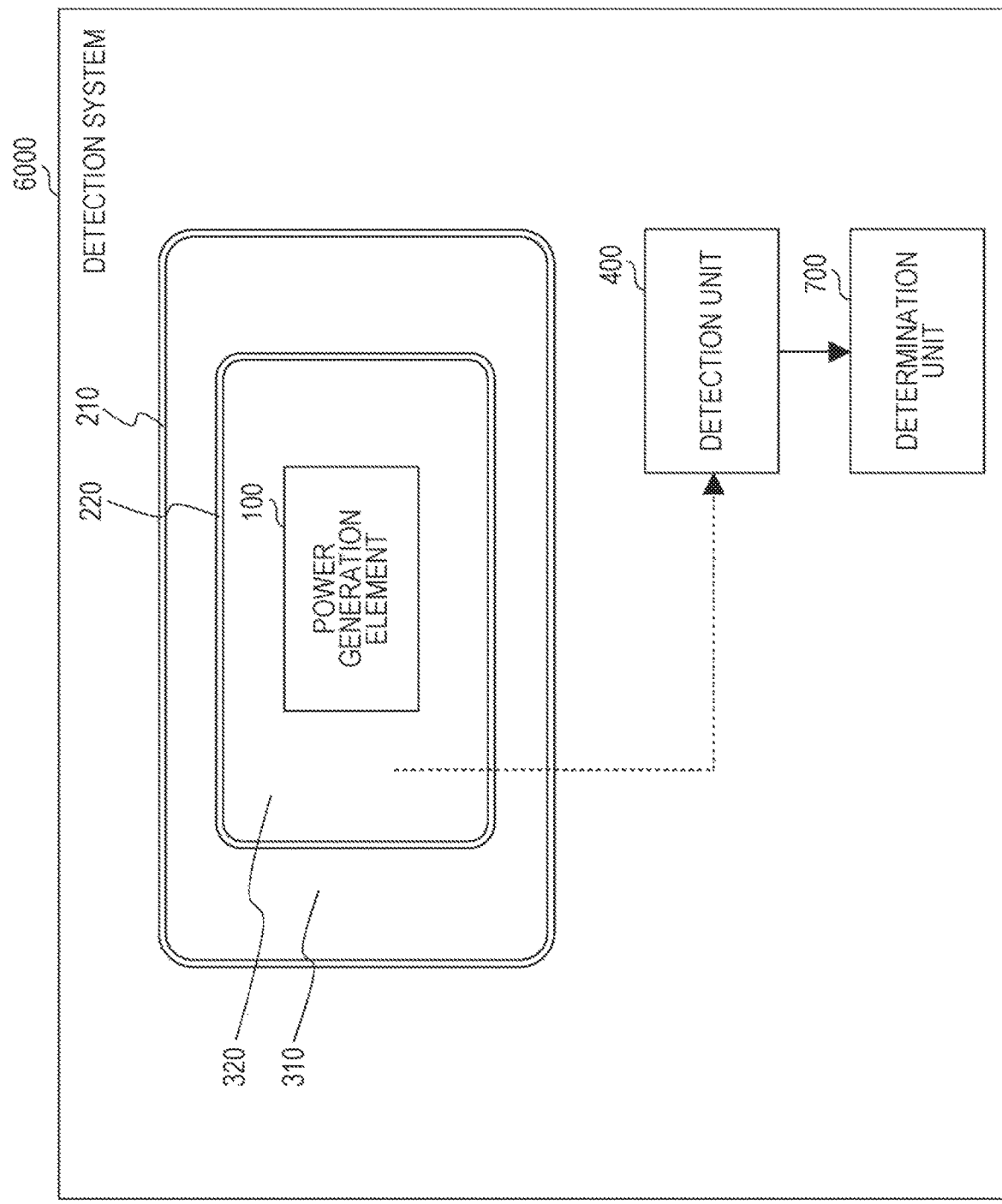
FIG. 26 illustrates a general configuration of a detection system according to a sixth embodiment.

FIG. 26 illustrates a general configuration of a detection system 6000 according to the sixth embodiment.

The detection system 6000 according to the sixth embodiment includes the following configuration in addition to the configuration of the detection system according to the above-described fifth embodiment.

That is, the detection system 6000 according to the sixth embodiment further includes a determination unit 700.

The determination unit 700 determines the breakage states of the first outer cover body 210 and the second outer cover body 220 on the basis of the detection result of the detection unit 400.

FIG. 27 illustrates a determination method of a determination unit 700 according to the sixth embodiment.

In the detection system 6000 according to the sixth embodiment, the determination unit 700 may execute the determination method shown in FIG. 27.

That is, if the detection result of the detection unit 400 indicates a state in which the outside atmosphere is not detected in the second space section 320 and the first gas is not detected in the second space section 320, the determination unit 700 determines that neither the first outer cover body 210 nor the second outer cover body 220 is broken (case A-50).

Also, if the detection result of the detection unit 400 indicates a state in which the outside atmosphere is not detected in the second space section 320 and the first gas is detected in the second space section 320, the determination unit 700 determines that the first outer cover body 210 is not broken and the second outer cover body 220 is broken (case C-50).

Also, if the detection result of the detection unit 400 indicates a state in which the outside atmosphere is detected in the second space section 320 and the first gas is detected in the second space section 320, the determination unit 700 determines that both the first outer cover body 210 and the second outer cover body 220 are broken (case D-50).

With the above-described configuration, the determination accuracy of the breakage state of the outer cover member enveloping the power generation element 100 can be increased. To be specific, the presence of breakage of only the second outer cover body 220 or both the first outer cover body 210 and the second outer cover body 220 can be individually determined on the basis of the detection result of the outside atmosphere and the detection result of the first gas in the second space section 320. Accordingly, the generation of breakage of the first outer cover body 210 and the second outer cover body 220 can be determined with high accuracy at an early stage.

It is to be noted that, in the detection system 6000 according to the sixth embodiment, the determination unit 700 may further execute the following determination method.

That is, if the detection result of the detection unit 400 indicates a state in which the outside atmosphere is detected in the second space section 320 and the first gas is not detected in the second space section 320, the determination unit 700 determines that both the first outer cover body 210 and the second outer cover body 220 are broken (case D-51).

With the above-described configuration, the determination accuracy of the breakage state of the outer cover member enveloping the power generation element 100 can be further increased. That is, by using the detection result in the case where at least the outside atmosphere is detected in the second space section 320, the presence of breakage of the first outer cover body 210 and the second outer cover body 220 can be determined even if it is difficult to detect the first gas (for example, if a failure of the detection unit 400 occurs or if the first gas is lost). Accordingly, the generation of breakage of the first outer cover body 210 and the second outer cover body 220 can be determined at an earlier stage.

It is to be noted that, in the detection system according to the fifth or sixth embodiment, the power generation element 100 may contain a material which contributes to generation of a generated gas.

In this case, the detection unit 400 may detect the generated gas in the second space section 320.

Respective components according to the sixth embodiment may properly use the respective components according to the above-described second embodiment.

The configurations described in any of the first to sixth embodiments may be mutually properly combined.

The detection system (battery system) of the present disclosure may be used as, for example, an on-vehicle detection system (battery system) including an all-solid lithium ion secondary battery.

What is claimed is:

1. A detection system comprising:
    a power generation element;
    a first outer cover body enveloping the power generation element;
    a second outer cover body located between the power generation element and the first outer cover body, and enveloping the power generation element;
    a first space section enclosed by the first outer cover body and the second outer cover body;
    a second space section enclosed by the second outer cover body; and
    a detection unit that detects a gas in the first space section and a gas in the second space section.

2. The detection system according to claim 1,
    wherein a first gas is encapsulated in the first space section,
    wherein the detection unit detects an outside atmosphere entering from outside of the first outer cover body, in the first space section, and
    wherein the detection unit detects the first gas in the second space section.

3. The detection system according to claim 2, further comprising:
    a determination unit that determines a breakage state of the first outer cover body and a breakage state of the second outer cover body on the basis of a detection result of the detection unit,
    wherein, if the detection result indicates a state in which the outside atmosphere is not detected in the first space section and the first gas is not detected in the second space section, the determination unit determines that neither the first outer cover body nor the second outer cover body is broken,
    wherein, if the detection result indicates a state in which the outside atmosphere is detected in the first space section and the first gas is not detected in the second space section, the determination unit determines that the first outer cover body is broken and the second outer cover body is not broken,
    wherein, if the detection result indicates a state in which the outside atmosphere is not detected in the first space section and the first gas is detected in the second space section, the determination unit determines that the first outer cover body is not broken and the second outer cover body is broken, and
    wherein, if the detection result indicates a state in which the outside atmosphere is detected in the first space section and the first gas is detected in the second space section, the determination unit determines that both the first outer cover body and the second outer cover body are broken.

4. The detection system according to claim 1,
    wherein a first gas is encapsulated in the first space section,
    wherein a second gas being a gas different from the first gas is encapsulated in the second space section,
    wherein the detection unit detects an outside atmosphere entering from outside of the first outer cover body and the second gas, in the first space section, and
    wherein the detection unit detects the first gas in the second space section.

5. The detection system according to claim 4, further comprising:
    a determination unit that determines a breakage state of the first outer cover body and a breakage state of the second outer cover body on the basis of a detection result of the detection unit,
    wherein, if the detection result indicates a state in which the outside atmosphere is not detected in the first space section, the second gas is not detected in the first space section, and the first gas is not detected in the second space section, the determination unit determines that neither the first outer cover body nor the second outer cover body is broken,
    wherein, if the detection result indicates a state in which the outside atmosphere is detected in the first space section, the second gas is not detected in the first space section, and the first gas is not detected in the second space section, the determination unit determines that the first outer cover body is broken and the second outer cover body is not broken,
    wherein, if the detection result indicates a state in which the outside atmosphere is not detected in the first space section, the second gas is detected in the first space section, and the first gas is detected in the second space section, the determination unit determines that the first outer cover body is not broken and the second outer cover body is broken, and
    wherein, if the detection result indicates a state in which the outside atmosphere is detected in the first space section, the second gas is detected in the first space section, and the first gas is detected in the second space section, the determination unit determines that both the first outer cover body and the second outer cover body are broken.

6. The detection system according to claim 5,
    wherein, if the detection result indicates a state in which the outside atmosphere is not detected in the first space section, and the second gas is detected in the first space section and/or the first gas is detected in the second space section, the determination unit determines that the first outer cover body is not broken and the second outer cover body is broken, and wherein, if the detection result indicates a state in which the outside atmosphere is detected in the first space section, and the second gas is detected in the first space section and/or the first gas is detected in the second space section, the determination unit determines that both the first outer cover body and the second outer cover body are broken.

7. The detection system according to claim 4,
wherein the detection unit detects the first gas and the outside atmosphere in the second space section.

8. The detection system according to claim 7, further comprising:
a determination unit that determines a breakage state of the first outer cover body and a breakage state of the second outer cover body on the basis of a detection result of the detection unit,
wherein, if the detection result indicates a state in which the outside atmosphere is not detected in the first space section, the second gas is not detected in the first space section, the first gas is not detected in the second space section, and the outside atmosphere is not detected in the second space section, the determination unit determines that neither the first outer cover body nor the second outer cover body is broken,
wherein, if the detection result indicates a state in which the outside atmosphere is detected in the first space section, the second gas is not detected in the first space section, the first gas is not detected in the second space section, and the outside atmosphere is not detected in the second space section, the determination unit determines that the first outer cover body is broken and the second outer cover body is not broken,
wherein, if the detection result indicates a state in which the outside atmosphere is not detected in the first space section, the second gas is detected in the first space section, the first gas is detected in the second space section, and the outside atmosphere is not detected in the second space section, the determination unit determines that the first outer cover body is not broken and the second outer cover body is broken, and
wherein, if the detection result indicates a state in which the outside atmosphere is detected in the first space section, the second gas is detected in the first space section, the first gas is detected in the second space section, and the outside atmosphere is detected in the second space section, the determination unit determines that both the first outer cover body and the second outer cover body are broken.

9. The detection system according to claim 8,
wherein, if the detection result indicates a state in which the outside atmosphere is detected in the first space section and the outside atmosphere is detected in the second space section, the determination unit determines that both the first outer cover body and the second outer cover body are broken.

10. The detection system according to claim 1, further comprising:
a first sensor element,
wherein the first sensor element is arranged in the first space section, and wherein the detection unit detects the gas in the first space section on the basis of a detection signal from the first sensor element.

11. The detection system according to claim 1, further comprising:
a first communicating tube that causes the first space section to communicate with the detection unit,
wherein the detection unit detects the gas in the first space section introduced through the first communicating tube.

12. The detection system according to claim 1, further comprising:
a second sensor element,
wherein the second sensor element is arranged in the second space section,
wherein the detection unit detects the gas in the second space section on the basis of a detection signal from the second sensor element,
wherein a portion of the first outer cover body and a portion of the second outer cover body are integrated with one another and form a common outer cover portion,
wherein the second sensor element includes a second connection line, and
wherein the second connection line extends through the common outer cover portion and is connected with the detection unit.

13. The detection system according to claim 1, further comprising:
a second communicating tube that causes the second space section to communicate with the detection unit,
wherein the detection unit detects the gas in the second space section introduced through the second communicating tube,
wherein a portion of the first outer cover body and a portion of the second outer cover body are integrated with one another and form a common outer cover portion, and
wherein the second communicating tube is coupled with the common outer cover portion.

14. The detection system according to claim 1,
wherein the power generation element contains a material which contributes to generation of a generated gas, and
wherein the detection unit detects the generated gas in the first space section and the generated gas in the second space section.

15. The detection system according to claim 14, further comprising:
a determination unit that determines a breakage state of the second outer cover body on the basis of a detection result of the detection unit,
wherein, if the detection result indicates a state in which the generated gas is not detected in the first space section and the generated gas is detected in the second space section, the determination unit determines that the second outer cover body is not broken, and
wherein, if the detection result indicates a state in which the generated gas is detected in the first space section and the generated gas is detected in the second space section, the determination unit determines that the second outer cover body is broken.

* * * * *